(12) United States Patent
Shiibashi et al.

(10) Patent No.: US 7,092,970 B2
(45) Date of Patent: Aug. 15, 2006

(54) MEDICAL IMAGE RADIOGRAPHING SYSTEM, METHOD FOR MANAGING MEDICAL IMAGE AND METHOD FOR DISPLAYING MEDICAL IMAGE

(75) Inventors: Takao Shiibashi, Hachioji (JP); Naoto Moriyama, Hachioji (JP); Wataru Motoki, Hachioji (JP)

(73) Assignee: Konica Minolta Holdings, Inc., Tokyo (JP)

( * ) Notice: Subject to any disclaimer, the term of this patent is extended or adjusted under 35 U.S.C. 154(b) by 187 days.

(21) Appl. No.: 10/789,521

(22) Filed: Feb. 27, 2004

(65) Prior Publication Data

US 2004/0240624 A1 Dec. 2, 2004

(30) Foreign Application Priority Data

Mar. 26, 2003 (JP) ............................. 2003-084836
Mar. 28, 2003 (JP) ............................. 2003-092443

(51) Int. Cl.
*G06F 17/00* (2006.01)
(52) U.S. Cl. .................................. 707/104.1; 382/132
(58) Field of Classification Search ............. 707/104.1, 707/200, 10; 382/132, 128, 313
See application file for complete search history.

(56) References Cited

U.S. PATENT DOCUMENTS

| | | | | |
|---|---|---|---|---|
| 5,615,112 A * | 3/1997 | Liu Sheng et al. | ....... | 707/104.1 |
| 5,960,443 A * | 9/1999 | Young et al. | ............ | 707/104.1 |
| 6,611,846 B1 * | 8/2003 | Stoodley | ................. | 707/104.1 |
| 6,678,703 B1 * | 1/2004 | Rothschild et al. | ......... | 707/201 |
| 6,806,487 B1 * | 10/2004 | Tamakoshi et al. | ......... | 250/586 |
| 6,819,785 B1 * | 11/2004 | Vining et al. | ............... | 382/128 |
| 6,820,100 B1 * | 11/2004 | Funahashi | ................... | 707/204 |
| 6,920,465 B1 * | 7/2005 | Motoki | ..................... | 707/104.1 |
| 6,954,767 B1 * | 10/2005 | Kanada | ....................... | 707/204 |
| 2004/0086164 A1 * | 5/2004 | Moriyama et al. | .......... | 382/131 |
| 2004/0089710 A1 * | 5/2004 | Moriyama | .................. | 235/375 |

FOREIGN PATENT DOCUMENTS

JP 2000-107160 A 4/2000

OTHER PUBLICATIONS

Freedman et al., Image Processing of Medical Radiographs for a Single Image Display, Image Processing and Its Applications, 1997, Sixth International Conference on, vol. 1, Jul. 14-17, 1997, pp. 12-16.*

* cited by examiner

*Primary Examiner*—Greta Robinson
(74) *Attorney, Agent, or Firm*—Frishauf, Holtz, Goodman & Chick, P.C.

(57) ABSTRACT

A medical image radiographing system has: a radiographic-room-use radiographing apparatus for performing medical radiography in a radiographic room; a portable radiographing apparatus for performing medical radiography at a bedside of the patient; and a controller for displaying an input screen and for inputting information through the input screen, wherein, when radiographing order information is inputted, the controller displays a selection input screen for inputting selection of whether the radiographing order information is for one by the radiographic-room-use radiographing apparatus or one by the portable radiographing apparatus, and displays a radiographing order information input screen different according to the selection, and at input completion of the radiographing order information, the controller displays a confirmation input screen for inputting confirmation of the input completion regardless of the one by the radiographic-room-use radiographing apparatus or the one by the portable radiographing apparatus.

25 Claims, 28 Drawing Sheets

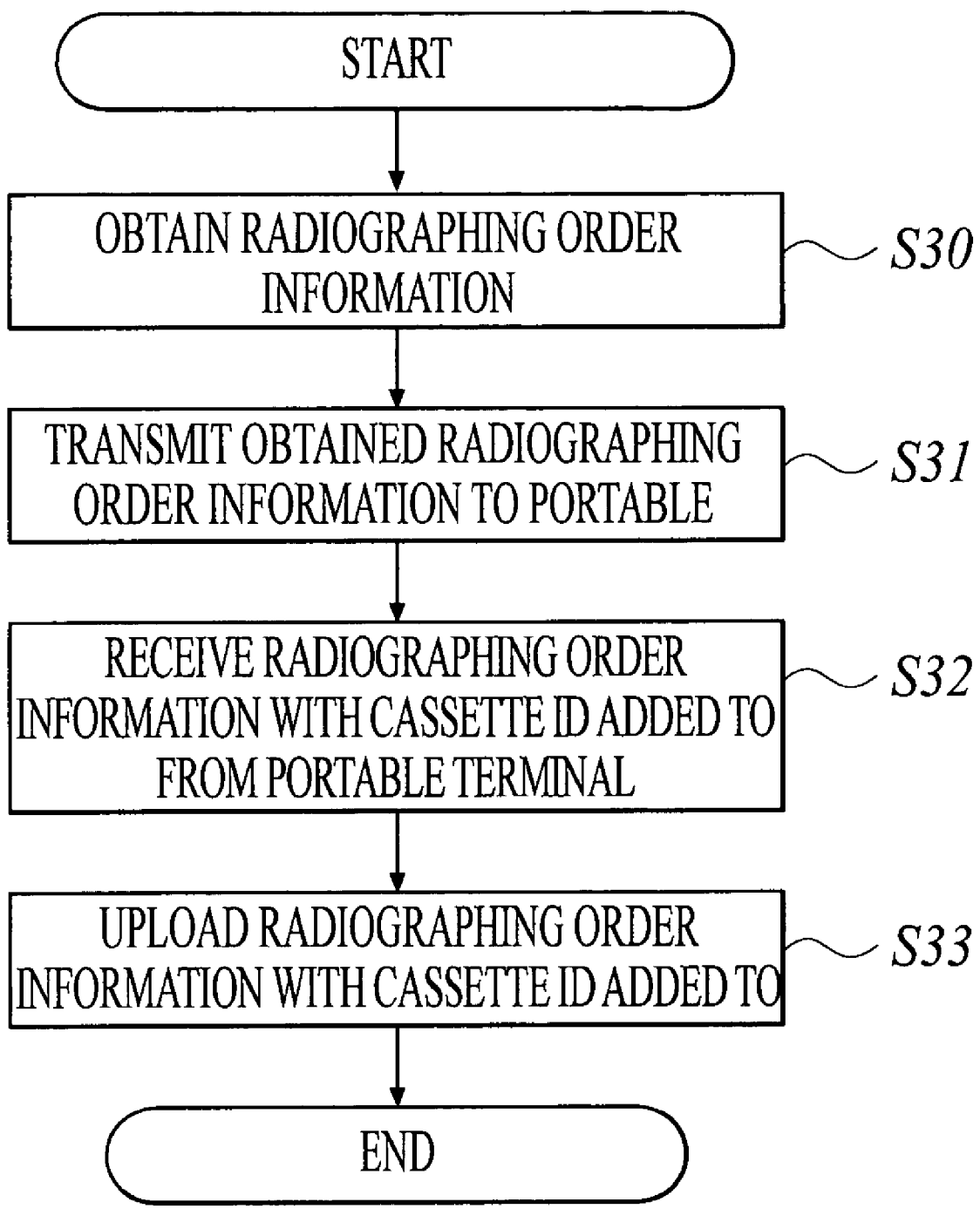

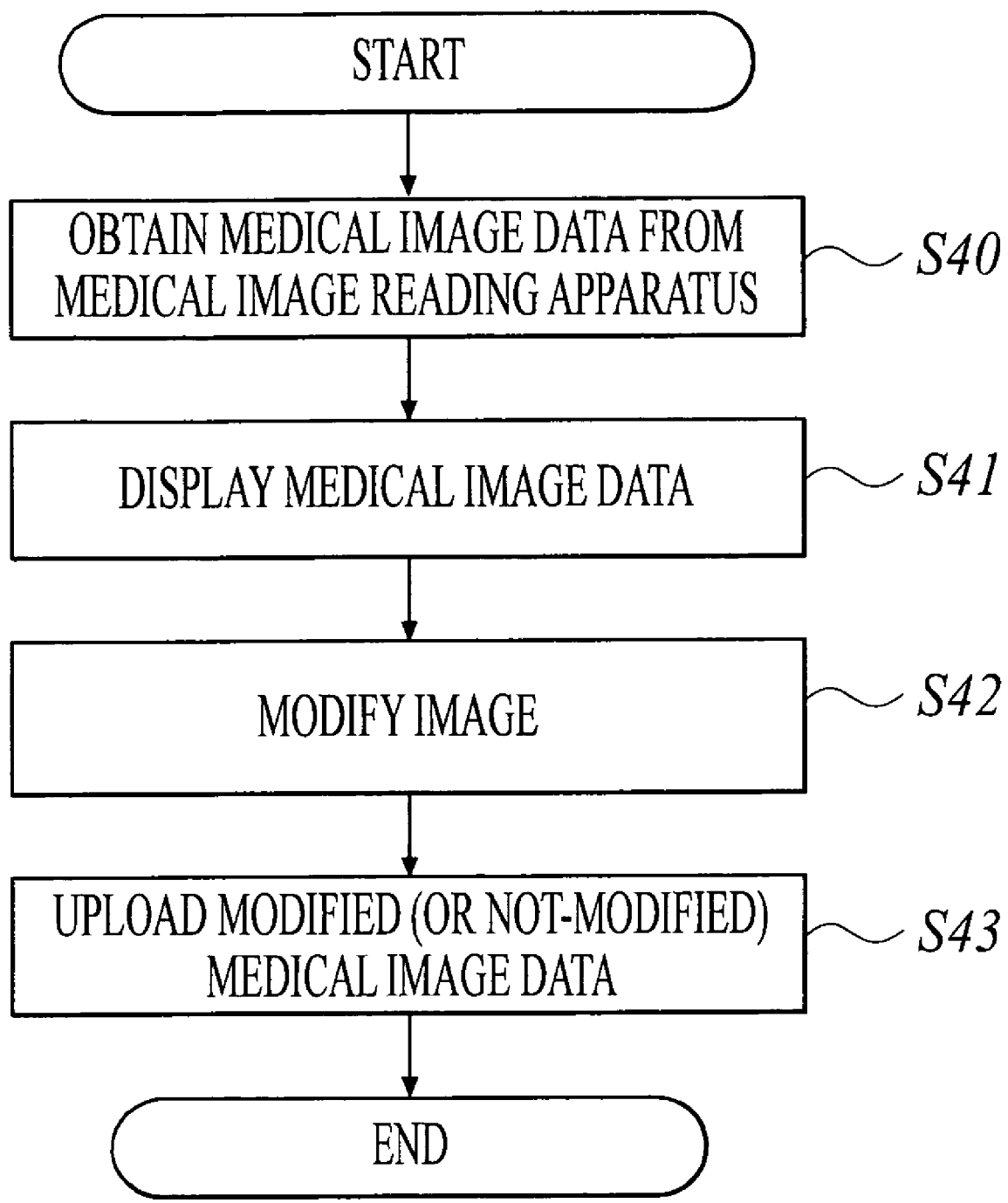

FIG.9A

| PATIENT ID | PATIENT NAME | HOSPITAL ROOM |
|---|---|---|
| 0001 | ICHIRO YAMADA | |
| 12345 | TARO SAKURA | |

0/2  ALL

PATIENT ID 0001  ICHIRO YAMADA
SEX M  AGE
HOSPITAL WARD  HOSPITAL ROOM

01/02

CHEST ETC OBLIQUE
0400010802016
CHEST ETC APICAL

CANCEL  OK

OPERATOR:

| PATIENT ID | 01212 | | SEX | MALE |
|---|---|---|---|---|
| PATIENT NAME ROMAN ALPHABET | SAKURA TAROU | | BIRTH DATE (AGE) | 1993-04-23 O'CLOCK MINUTE SECOND (10 YEARS 10 MONTHS OLD) |
| PATIENT NAME KANA | サクラ タロウ | | BIRTH DATE (WITHOUT CLOCK) | 1993-04-23 (10 YEARS 10 MONTHS OLD) |
| PATIENT NAME CHINESE CHARACTER | 桜 太郎 | | PATIENT COMMENTS | |

1/4  ◁ ▷

(SEARCH)

ABC/abc  keyboard

| a | b | c | d | e | f | g | _ |
| h | i | j | k | l | m | n | @ | DEL | BS |
| o | p | q | r | s | t | u | " |
| v | w | x | y | z | # | , | ; | ↓ | ↑ |
| Caps Lock | [Space] | & | ENTER |

CLEAR  CANCEL  OK

| OPERATOR:TARO SUZUKI | FILTER | | | | SCHEDULE [2] ITEM | SUSPEND [0] ITEM | 635 |
|---|---|---|---|---|---|---|---|
| PATIENT ID [1]▽ | TRANSMISSION TAB [3]▽ | PATIENT NAME [1]▽ | SEX | BIRTH DATE | RADIOGRAPHING CONDITION | RADIOGRAPHING COUNT | SUSPEND |
| 03434 | | ICHIRO YAMADA | MALE | / / | SKULL-AP | 0/2 | SUSPENDED |
| 01212 | | TARO SAKURA | MALE | / / | INFANT CHEST-AP | 0/2 | SUSPENDED |

◁◁ ◁ ▷ ▷▷

SELECT ALL

TRANSMIT

RECEIVE

NEW/SEARCH | MODIFY | DELETE | SET CONDITION | SELECTING CONDITION | REFRESH | CONFIRMATION SCREEN

| PORTABLE DESIGNATION | PATIENT ID | TAB TYPE | PATIENT NAME | SEX | BIRTH DATE | RADIOGRAPHING CONDITION | RADIOGRAPHY COUNT | SUSPEND |
|---|---|---|---|---|---|---|---|---|
| ON | 0001 | | ICHIRO YAMADA | MALE | / / | CHEST ETC OBLIQUE-P→A | 0/2 | SUSPENDED |
| ON | 12345 | | TARO SAKURA | MALE | / / | INFANT CHEST-P-A | 0/2 | SUSPENDED |
| OFF | 0002 | | JIRO YAMADA | MALE | / / | CHEST ETC OBLIQUE-P→A | 0/2 | SUSPENDED |
| OFF | 0003 | | HANAKO SAKURA | FEMALE | / / | INFANT CHEST-P-A | 0/2 | SUSPENDED |

OPERATOR:TARO SUZUKI  FILTER  SCHEDULE 2  ITEM  SUSPEND 0 ITEM

NEW/SEARCH | MODIFY | DELETE | 10X10 REPAIR | EXTRACTION CONDITION | REFRESH

PORTABLE DESIGNATION | DISK | | SELECT ALL | TRANSMIT | RECEIVE | CONFIRMATION SCREEN

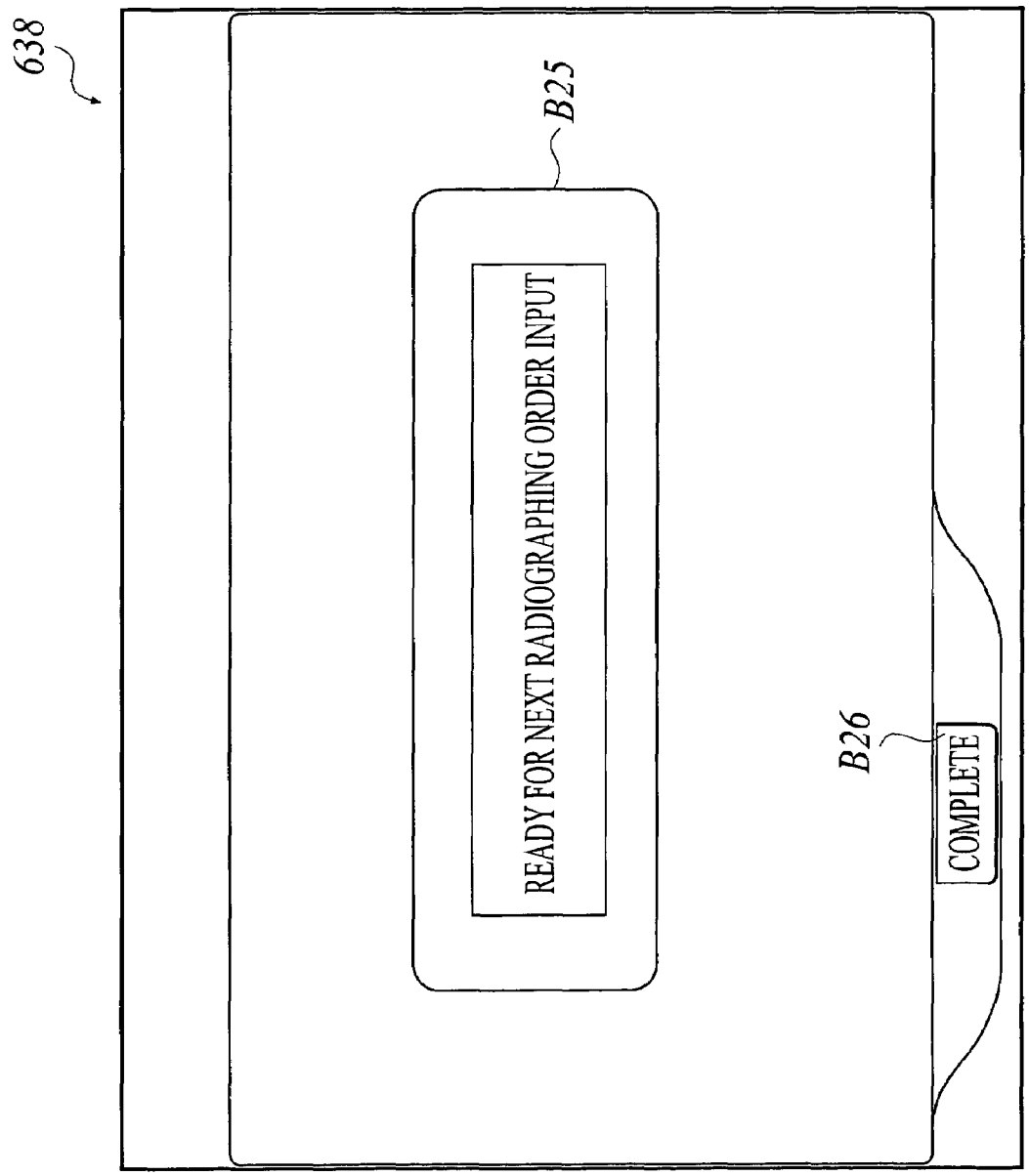

| RADIOGRAPHING ID | PATIENT ID | NAME | SEX | AGE | HOSPITAL ROOM | DEPARTMENT OF REQUEST | RADIOGRAPHIC PART | RADIOGRAPHING APPARATUS | RADIOGRAPHING COUNT | CASSETTE ID |
|---|---|---|---|---|---|---|---|---|---|---|
| 2002101001 | 1000002 | ○○○○ | MALE | 40 | 101 | SURGERY | SKULL A→P | A | 3 | |
| 2002101002 | 1000002 | ○○○○ | MALE | 40 | 101 | SURGERY | CHEST R→L | A | 4 | |
| 2002101003 | 1000005 | △△△△ | FEMALE | 50 | 205 | INTERNAL MEDICINE | ABDOMEN LAT | B | 5 | |
| 2002101004 | 1000005 | △△△△ | FEMALE | 50 | 205 | INTERNAL MEDICINE | ABDOMEN P→A | B | 5 | |
| ... | ... | ... | ... | ... | ... | ... | ... | ... | ... | ... |

161

MEDICAL IMAGE RADIOGRAPHING SYSTEM, METHOD FOR MANAGING MEDICAL IMAGE AND METHOD FOR DISPLAYING MEDICAL IMAGE

BACKGROUND OF THE INVENTION

1. Field of the Invention

The present invention relates to a medical image radiographing system, a method for managing a medical image and a method for displaying a medical image.

2. Description of Related Art

Recently, a medical image radiographing system comprising a radiographing apparatus such as a CR (Computed Radiography) apparatus or the like for obtaining as digital image data, a radiation image widely used as a medical image has been developed.

In the above-mentioned radiographing apparatus, for example, a radiation image conversion panel in which a photostimulable phosphor layer is formed (hereinafter, it is called an imaging plate) is used. The imaging plate accumulates radiation energy corresponding to the degree of radiation transmission through each part of a subject, and emits the accumulated radiation energy as fluorescence by being irradiated by excitation light such as infrared ray or the like. A photoelectric converter such as semiconductor or the like photoelectrically converts light signals of the fluorescence into radiation image signals. The radiation image obtained in such a way, after being applied image processing on, is visualized on film, a display device or the like, or is stored along with patient information in a database to be used for various medical practice.

Based on radiographing order information from HIS (Hospital Information System) or RIS (Radiology Information System) each managing examination information in hospital facilities or in a department of radiology, a radiographic operator performs radiography with the use of the above-mentioned radiographing apparatus (hereinafter, it is called a radiographic-room-use radiographing apparatus) that is installed in a radiographic room.

In particular, recently, a traveling-type radiographing apparatus (hereinafter, it is called a portable radiographing apparatus) capable of radiographing at a bedside in a hospital room that holds a patient has been achieved (for example, see Japanese Patent Application Publication (Unexamined) No. Tokukai 2000-107160). With the use of the portable radiographing apparatus, it is possible to easily perform radiographing on a patient who is not able to travel to a radiographic room because he/she has difficulty in walking due to severe illness/injury. Further, if a medical image reading apparatus for reading a radiation image from the imaging plate is installed in a predetermined place at each floor, a nurse station or the like, it is possible for a radiographic operator to easily confirm a radiography result without traveling among floors. Here, the above-mentioned imaging plate is stored in a dedicated case, the so-called cassette, and unique identification number is allocated to each cassette and/or each imaging plate. According to the identification number, a cassette and/or an imaging plate can be identifiable.

The medical image radiographed in the above-described medical image radiographing system is read by the medical image reading apparatus, and stored in a controller with correspondence to radiographing order information. The radiographing order information includes information regarding patient (hereinafter, it is referred to as "patient information") such as name, sex and the like of a patient to be radiographed, and information regarding radiography (hereinafter, it is referred to as "radiography information") such as a radiographic part, a radiographing method and the like, and has therein an instruction such as, on which patient, how radiography should be performed, or the like. Then, the read medical image is displayed on a display unit of the controller with the radiographing order information correspondingly, and the controller applies an image process suitable for diagnosis on the medical image. With reference to FIG. 18, an image process screen in an earlier art will be described.

As shown in FIG. 18, in an image process screen 640, a plurality of medical images radiographed per one patient are displayed in the same screen. In other words, in the image process screen 640, placed are an area for displaying therein patient information of one patient, an area for displaying therein the plurality of medical images radiographed per one patient, and an area for displaying therein radiography information corresponding to each medical image, and in the same screen, as many as four types of medical images can be displayed. Concretely, in the area located at the upper part of the screen for displaying therein the patient information, placed are items for displaying patient ID, name, sex, date of birth, and in each area thereof, corresponding data is displayed. In the area located at the center of the screen for displaying therein a medical image, placed are an area for displaying therein a medical image and items for displaying identification information of a radiographing apparatus and resolution of an image. Further, the area located bottom of the screen for displaying therein the radiography information, placed are items for displaying a radiographic part and a cassette ID.

By the way, in the above-mentioned earlier art, there is a problem as following. There is a case where the same radiographic operator all at once inputs a plurality of radiographing order information regardless of the cases of, radiography with the use of the radiographing apparatus for a radiographic room fixedly installed in a radiographic room (hereinafter, it is called normal radiography) and radiography with the use of the portable radiographing apparatus (hereinafter, it is called portable radiography). In such a case, since the content that the radiographic operator is currently inputting differs between normal radiography and portable radiography, it is not clear for the radiographic operator to recognize the content. The more number of patients, the more complicated the input of radiographing order information becomes, and therefore there is a possibility of causing unexpected contingency such as an input mistake or the like.

In addition, in the medical image radiographing system in the earlier art, radiography in a radiographic room is performed on each patient, and each time of finishing a set of the radiography on one patient, medical images are obtained to be displayed on a monitor or the like. Thereby, in the image process screen, it is suitable to use a structure where a plurality of medical images are displayed on the monitor at each patient for benefiting from performing an image process all at once. However, when radiographing a medical image is performed at round visits with the use of the traveling-capable radiographing apparatus, in most cases, radiography on a plurality of patients is performed at one round visit for improving operating effectiveness. Thereby, as mentioned above, when medical images radiographed per each patient are to be displayed, it is necessary to display medical images of each of the plurality of patients respectively. Consequently, there is a problem where, if the number of patients increases, operation becomes more complicated and operationality becomes worse.

SUMMARY OF THE INVENTION

An object of the present invention is to sufficiently minimize an input mistake of radiographing order information and, in the case of displaying medical images of a plurality of patients, to provide a medical image radiographing system, a method for managing a medical image and a method for displaying a medical image each displaying the medical images with good visibility and operationality.

In accordance with a first aspect of the present invention, a medical image radiographing system comprises: a radiographic-room-use radiographing apparatus for performing medical radiography on a predetermined part of a patient in a radiographic room; a portable radiographing apparatus capable of moving and for performing medical radiography on a predetermined part of the patient at a bedside of the patient; and a controller for displaying an input screen corresponding to inputted information and for inputting information through the input screen, wherein, when radiographing order information for performing the medical radiography is inputted, the controller displays a selection input screen for inputting selection of whether the radiographing order information is for the medical radiography performed by the radiographic-room-use radiographing apparatus or the medical radiography performed by the portable radiographing apparatus, and displays a radiographing order information input screen different according to a content of the selection inputted, and at input completion of the radiographing order information, the controller displays a confirmation input screen for inputting confirmation of the input completion of the radiographing order information regardless of whether the radiographing order information is for the medical radiography performed by the radiographic-room-use radiographing apparatus or the medical radiography performed by the portable radiographing apparatus.

In accordance with a second aspect of the present invention, a method for managing a medical image with a medical image radiographing system comprising a radiographic-room-use radiographing apparatus for performing medical radiography on a predetermined part of a patient in a radiographic room, a portable radiographing apparatus capable of moving and for performing medical radiography on a predetermined part of the patient at a bedside of the patient, and a controller for displaying an input screen corresponding to inputted information and for inputting information through the input screen, comprises: displaying, when radiographing order information is inputted for performing the medical radiography, a selection input screen for inputting selection of whether the radiographing order information is for the medical radiography performed by the radiographic-room-use radiographing apparatus or the medical radiography performed by the portable radiographing apparatus; displaying a radiographing order information input screen different according to a content of the selection inputted; and displaying, at input completion of the radiographing order information, a confirmation input screen for inputting confirmation of the input completion of the radiographing order information regardless of whether the radiographing order information is for the medical radiography performed by the radiographic-room-use radiographing apparatus or the medical radiography performed by the portable radiographing apparatus.

According to the system of the first aspect and the method of the second aspect of the present invention, when radiographing order information is to be inputted, regardless of both the case of normal radiography with the use of a radiographing apparatus for a radiographic room, which is fixedly installed in a radiographic room and the case of portable radiography with the use of a portable radiographing apparatus, it is possible to input radiographing order information by approximately the same input operations. Moreover, even in the case that an identical radiographic operator input both radiographing order information for normal radiography and radiographing order information for portable radiography all at once, or in the case that the input of radiographing order information is very complicated due to the large number of patients, it is easy for a radiographic operator to recognize the content that he/she is inputting currently during the whole work flow, and thereby it is sufficiently possible to avoid unexpected contingency such as an input mistake or the like at both normal radiography and portable radiography.

Preferably, in the system of the first aspect of the present invention, the radiographing order information input screen is an input screen for inputting the radiographing order information including a radiographing condition of the patient.

Preferably, in the method of the second aspect of the present invention, the radiographing order information input screen is an input screen for inputting the radiographing order information including a radiographing condition of the patient.

Preferably, in the system of the first aspect of the present invention, when the selection inputted is in regard to the portable radiographing apparatus, the controller displays the input screen for inputting the radiographing condition, which is displayed when the selection inputted is in regard to the radiographic-room-use radiographing apparatus, with effect added on, the effect indicating that use of the portable radiographing apparatus is not applicable, as the radiographing order information input screen.

Preferably, in the method of the second aspect of the present invention, the displaying a radiographing order information includes displaying, when the selection inputted is in regard to the portable radiographing apparatus, the input screen for inputting the radiographing condition, which is displayed when the selection inputted is in regard to the radiographic-room-use radiographing apparatus, with effect added on, the effect indicating that use of the portable radiographing apparatus is not applicable, as the radiographing order information input screen.

Preferably, in the apparatus of the first aspect of the present invention, when the selection inputted is in regard to the portable radiographing apparatus, the controller displays the input screen for inputting the radiographing condition, which is displayed when the selection inputted is in regard to the radiographic-room-use radiographing apparatus, with the radiographing condition meshed, the radiographing condition under which the use of the portable radiographing apparatus is not applicable, as the radiographing order information input screen.

Preferably, in the method of the second aspect of the present invention, the displaying a radiographing order information includes displaying, when the selection inputted is in regard to the portable radiographing apparatus, the input screen for inputting the radiographing condition, which is displayed when the selection inputted is in regard to the radiographic-room-use radiographing apparatus, with the radiographing condition meshed, the radiographing condition under which use of the portable radiographing apparatus is not applicable, as the radiographing order information input screen.

In accordance with a third aspect of the present invention, a medical image radiographing system comprises: a controller for managing radiographing order information and a medical image so as to correspond to each other; a portable terminal for storing the radiographing order information and identification information of a cassette so as to correspond to each other; and a medical image reading apparatus for reading out the medical image from a cassette and the identification information of the cassette, wherein the controller, the portable terminal and the medical image reading apparatus are connected through a network, the portable terminal comprises: a storage section for storing the radiographing order information and the identification information of the cassette so as to correspond to each other; and a communication section for transmitting the radiographing order information and the identification information of the cassette so as to correspond to each other; the medical image reading apparatus comprises: a communication section for transmitting the medical image read out from the cassette and the identification information of the cassette so as to correspond to each other, and the controller comprises: a communication section for receiving a set of the radiographing order information and the identification information of the cassette, and a set of the identification information of the cassette and the medical image; a storage section for storing the radiographing order information and the medical image so as to correspond to each other based on the identification information of the cassette; and a display control section for displaying at least two medical images over a plurality of patients among medical images corresponding to the radiographing order information received from a same portable terminal, on a same screen.

In accordance with a fourth aspect of the present invention, a method for displaying a medical image in a medical image radiographing system in which a controller for managing radiographing order information and the medical image so as to correspond to each other, a portable terminal for storing the radiographing order information and identification information of a cassette so as to correspond to each other and a medical image reading apparatus for reading out the medical image from the cassette and the identification information of the cassette are connected through a network, comprises: storing the radiographing order information and the identification information of the cassette so as to correspond to each other; transmitting the radiographing order information and the identification information of the cassette so as to correspond to each other; transmitting the medical image read out from the cassette and the identification information of the cassette so as to correspond to each other; receiving a set of the radiographing order information and the identification information of the cassette, and a set of the medical image and the identification information of the cassette; storing the radiographing order information and the medical image so as to correspond to each other based on the identification information of the cassette; displaying at least two medical images over a plurality of patients among medical images corresponding to the radiographing order information received from a same portable terminal, on a same screen.

According to the apparatus of the third aspect or the method of the fourth aspect of the present invention, since the medical images corresponding to the radiographing order information stored in the same portable terminal are displayed on the same screen, for example, in the case of radiographing medical images with the use the portable terminal at round visits, it is possible to display the medical images radiographed at the same round visits on the same screen. Thereby, an operator is able to perform the image processing on the radiographed medical images immediately.

Preferably, in the apparatus of the third aspect of the present invention, in the controller, the communication section receives a set of the radiographing order information of a plurality of patients and the identification information of the cassette, and a set of the medical images of the plurality of patients and the identification information of the cassette; the storage section stores the radiographing order information of the plurality of patients and the medical images of the plurality of patients so as to correspond to each other based on the identification information of the cassette; and the display control section displays at least two medical images over the plurality of patients among the medical images corresponding to the radiographing order information of the plurality of patients received from the same portable terminal, on the same screen.

Preferably, the method of the fourth aspect of the present invention further comprises: receiving a set of the radiographing order information of a plurality of patients and the identification information of the cassette, and set of the medical images of the plurality of patients and the identification information of the cassette; storing the radiographing order information of the plurality of patients and the medical images of the plurality of patients so as to correspond to each other based on the identification information of the cassette; and displaying at least two medical images over the plurality of patients among the medical images corresponding to the radiographing order information of the plurality of patients received from the same portable terminal, on the same screen.

According to the above-mentioned apparatus or the method, even in the case of performing radiography on a plurality of patient at round visits, since it is possible to display the medical images over the plurality of patients on the same screen, there is no need to have labor to display a medical image per each of the plurality of patients, and thereby it is possible to improve process efficiency.

Preferably, in the apparatus of the third aspect of the present invention, the controller comprises a mode setting section for setting a normal mode under which the medical image radiographed in the radiographic room is displayed or a portable mode under which the medical image radiographed at round visits is displayed, and the display control section displays the medical image according to a mode set by the mode setting section.

Preferably, the method of the fourth aspect of the present invention further comprises: setting a normal mode under which the medical image radiographed in a radiographic room is displayed or a portable mode under which the medical image radiographed at round visits is displayed; and displaying the medical image by switching a display screen according to a mode set.

According to the above-mentioned apparatus or the method, since it is possible to display medical images under suitable display mode according to a radiography mode, it is possible to improve operating efficiency.

Preferably, in the apparatus of the third aspect of the present invention, the display control section of the controller displays the medical image of a same patient on the same screen under the normal mode, and the display control section of the controller displays the medical image corresponding to the radiographing order information stored in a same portable terminal under the portable mode.

Preferably, in the method of the fourth aspect of the present invention, the displaying the medical image by switching a display screen according to a mode set includes displaying the medical image of a same patient on the same screen under the normal mode, and displaying the medical image corresponding to the radiographing order information stored in the same portable terminal on the same screen under the portable mode.

According to the above-mentioned apparatus or the method, for example, in the case of performing radiography in a normal radiographic room, it is possible to perform radiography per each patient and display a medical image per each patient on the same screen. Thereby, it is possible to relatively compare medical images regarding the same patient, and therefore it is convenient. On the other hand, in the case of performing radiography at round visits, since it is possible to display medical images corresponding to radiographing order information stored in the portable terminal used at the same round visits, over a plurality of patients on the same screen, it is user-friendly. Further, since it is possible to recognize a radiography mode according to a display mode of a medical image, an operator is able to operate the image process while clearly recognizing whether the displayed medical image is radiographed in a radiographic room or at round visits, and thereby it is user-friendly.

Preferably, in the apparatus of the third aspect of the present invention, in the portable terminal, the storage section stores the radiographing order information regarding the radiography at the round visits and the identification information of the cassette; and the communication section transmits the radiographing order information regarding the radiography at the round visits and the identification information of the cassette, and in the controller, the communication section receives the radiographing order information regarding the radiography at the round visits and the identification information of the cassette; the mode setting section sets the portable mode when the communication section receives the radiographing order information regarding the radiography at the round visits and the identification information of the cassette; and the display control section displays the medical image under the portable mode.

Preferably, the method of the fourth aspect of the present invention further comprises: storing the radiographing order information regarding the radiography at the round visits and the identification information; transmitting the radiographing order information regarding the radiography at the round visits and the identification information; receiving the radiographing order information regarding the radiography at the round visits and the identification information; setting the portable mode when the radiographing order information regarding the radiography at the round visits and the identification information are received; and displaying the medical image under the portable mode.

According to the above-mentioned apparatus or the method, when radiographing order information and identification information of a cassette are received from the portable terminal, the controller sets a mode to the portable mode, and displays medical images in a display form according to the portable mode. Thereby, since an operator is able to omit labor for setting a mode and it is possible to display a medical image under a suitable mode according to a radiography mode, it is convenient.

In accordance with a fifth aspect of the present invention, a medical image radiographing system comprises: a controller for managing a medical image, identification information of a cassette and radiographing order information so as to correspond to each other; a portable terminal for storing the radiographing order information and the identification information of the cassette so as to correspond to each other; and a medical image reading apparatus for reading out the medical image from the cassette and the identification information of the cassette, wherein the controller, the portable terminal and the medical image reading apparatus are connected through a network, the portable terminal comprises: a storage section stores the radiographing order information and the identification information of the cassette so as to correspond to each other; and a communication section for transmitting the radiographing order information and the identification information of the cassette so as to correspond to each other, the medical image reading apparatus comprises: a communication section for transmitting the medical image read out from the cassette and the identification information of the cassette so as to correspond to each other, and the controller comprises: a communication section for receiving a set of the radiographing order information and the identification information of the cassette, and a set of the medical image and the identification information of the cassette; a storage section for storing the radiographing order information and the medical image so as to correspond to each other based on the identification information of the cassette; a mode setting section for setting a normal mode under which the medical image radiographed in a radiographic room is displayed or a portable mode under which the medical image radiographed at round visits is displayed; and a display control section for displaying the medical image of a same patient on a same screen under the normal mode, and for displaying at least two medical images over a plurality of patients among medical images corresponding to the radiographing order information received from a same portable terminal, on the same screen.

In accordance with a sixth aspect of the present invention, a method for displaying a medical image in a medical image radiographing system in which a controller for managing the medical image, identification information of a cassette and radiographing order information so as to correspond to each other, a portable terminal for storing the radiographing order information and the identification information of the cassette so as to correspond to each other, and the medical image reading apparatus for reading out the medical image from the cassette and the identification information of the cassette are connected through a network, comprises: storing the radiographing order information and the identification information of the cassette so as to correspond to each other; transmitting the radiographing order information and the identification information of the cassette so as to correspond to each other; transmitting the medical image read out from the cassette and the identification information of the cassette so as to correspond to each other; receiving a set of the radiographing order information and the identification information of the cassette, and a set of the medical image and the identification information of the cassette; storing the radiographing order information and the medical image so as to correspond to each other based on the identification information of the cassette; setting a normal mode under which the medical image radiographed in a radiographic room is displayed or a portable mode under which the medical image radiographed at round visits is displayed; and displaying the medical image of a same patient on a same screen under the normal mode, and displaying at least two medical images over a plurality of patients among medical images corresponding to the radiographing order information received from a same portable terminal, on the same screen under the portable mode.

According to the apparatus of the fifth aspect or the method of the sixth aspect of the present invention, since it is possible to recognize a radiography mode according to a display mode of a medical image, an operator is able to perform the image process while clearly recognizing whether the displayed medical image is radiographed in a radiographic room or at round visits, and thereby it is user-friendly.

Preferably, in the apparatus of the fifth aspect of the present invention, in the controller, the communication section receives a set of a plurality of pieces of radiographing order information and the identification information of the cassette, and a set of a plurality of medical images and the identification information of the cassette; and the display control section displays all of the medical images corresponding to the plurality of pieces of radiographing order information received, on the same screen.

Preferably, the method of the sixth aspect of the present invention further comprises: receiving a set of a plurality of pieces of radiographing order information and the identification information of the cassette, and a set of a plurality of medical images and the identification information of the cassette; and displaying all of the medical images corresponding to the plurality of pieces of radiographing order information received, on the same screen.

According to the above-mentioned apparatus or the method, since it is possible to simultaneously confirm all the medical images radiographed at round visits, it is possible to minimize oversight on a medical image, misreception of radiographing order information, a lapse of radiography and the like.

Preferably, in the apparatus of the fifth aspect of the present invention, in the controller, the mode setting section sets the normal mode when the communication section does not receive the radiographing order information and the identification information of the cassette from the portable terminal, and sets the portable mode when the communication section receives the radiographing order information and the identification information of the cassette from the portable terminal; and the display control section displays the medical image according to a mode set by the mode setting section.

Preferably, the method of the sixth aspect of the present invention further comprises: setting the normal mode when the radiographing order information and the identification information of the cassette are not received, and setting the portable mode when the radiographing order information and the identification information of the cassette are received; and displaying the medical image according to a mode set.

According to the above-mentioned apparatus or the method, since a suitable mode is set by a mode setting section according to whether radiographing order information is received from the portable terminal, an operator is able to omit labor to set a mode, and it is possible to display a medical image easily and promptly.

In accordance with a seventh aspect of the present invention, a medical image radiographing system comprises: a radiographic-room-use radiographing apparatus for performing medical radiography on a predetermined part of a patient in a radiographic room; a portable radiographing apparatus capable of moving and for performing medical radiography on a predetermined part of the patient at a bedside of the patient; a controller for displaying an input screen corresponding to inputted information and for inputting information through the input screen; a portable terminal for storing radiographing order information and identification information of a cassette so as to correspond to each other; and a medical image reading apparatus for reading out the medical image from the cassette and the identification information of the cassette, wherein the controller comprises: a display section, when the radiographing order information for performing the medical radiography is inputted, for displaying a selection input screen for inputting selection of whether the radiographing order information is for the medical radiography performed by the radiographic-room-use radiographing apparatus or the medical radiography performed by the portable radiographing apparatus, displaying a radiographing order information input screen different according to a content of the selection inputted, and displaying, at input completion of the radiographing order information, a confirmation input screen for inputting confirmation of the input completion of the radiographing order information regardless of whether the radiographing order information is for the medical radiography performed by the radiographic-room-use radiographing apparatus or the medical radiography performed by the portable radiographing apparatus; a communication section for receiving a set of the radiographing order information and the identification information of the cassette, and a set of the medical image and the identification information of the cassette; a storage section for storing the radiographing order information and the medical image so as to correspond to each other based on the identification information of the cassette; and a display control section for displaying at least two medical images over a plurality of patients among medical images corresponding to the radiographing order information received from a same portable terminal, on a same screen, the portable terminal comprises: a storage section for storing the radiographing order information and the identification information of the cassette so as to correspond to each other; and a communication section for transmitting the radiographing order information and the identification information of the cassette so as to correspond to each other, and the medical image reading apparatus comprises: a communication section for transmitting the medical image read out from the cassette and the identification information of the cassette so as to correspond to each other.

BRIEF DESCRIPTION OF THE DRAWINGS

The present invention will become more fully understood from the detailed description given hereinafter and the accompanying drawing given by way of illustration only, and thus are not intended as a definition of the limits of the present invention, and wherein:

FIG. 7 is a flowchart illustrating a communication process executed by the controller 6 shown in FIG. 1, FIG. 8 is a flowchart illustrating an image process executed by the controller 6 shown in FIG. 1, FIG. 9A is one example of displaying patient names/IDs out of radiographing order information on a display screen of the portable terminal 4, FIG. 9B is one example of displaying a radiographing condition and a cassette ID out of the radiographing order information on the display screen of the portable terminal 4, FIG. 11 is one example of a screen displayed on the display screen of the controller 6 shown in FIG. 1, the screen to input patient information for portable radiography, FIG. 12 is one example of a screen displayed on the display screen of the controller 6 shown in FIG. 1, the screen to input a radiographing condition for portable radiography, FIGS. 13A, 13B and 13C are one example of displaying radiographing order information for portable radiography as a list on the display screen of the controller 6 shown in FIG. 1, FIG. 14 is one example of a screen displayed on the display screen of the controller 6 shown in FIG. 1, the screen to input a radiographing condition for normal radiography, FIG. 15 is one example of displaying radiographing order information for normal radiography as a list on the display screen of the controller 6 shown in FIG. 1, FIG. 16 is one example of a screen displayed on the display screen of the controller 6 shown in FIG. 1, the screen to inform the completion of inputting radiographing order information to one patient, FIG. 18 is one example of an image process screen under a normal mode displayed on the display screen of the controller 6 shown in FIG. 1, FIG. 21 is a view showing a data structure of a radiographing order information file 161 stored in the storage 160 shown in FIG. 20.

EMBODIMENTS OF THE INVENTION

First Embodiment

Hereinafter, with reference to figures, a first embodiment to which the present invention is applied will be described in detail. However, the scope of the invention is not limited to the illustrated examples. Here, in the following, as one example of an embodiment characteristic of the present invention, a medical image radiographing system which performs radiographing at round visits with the use of a portable terminal, which is carriageable, and a traveling-capable radiographing apparatus will be described.

Figure 1:
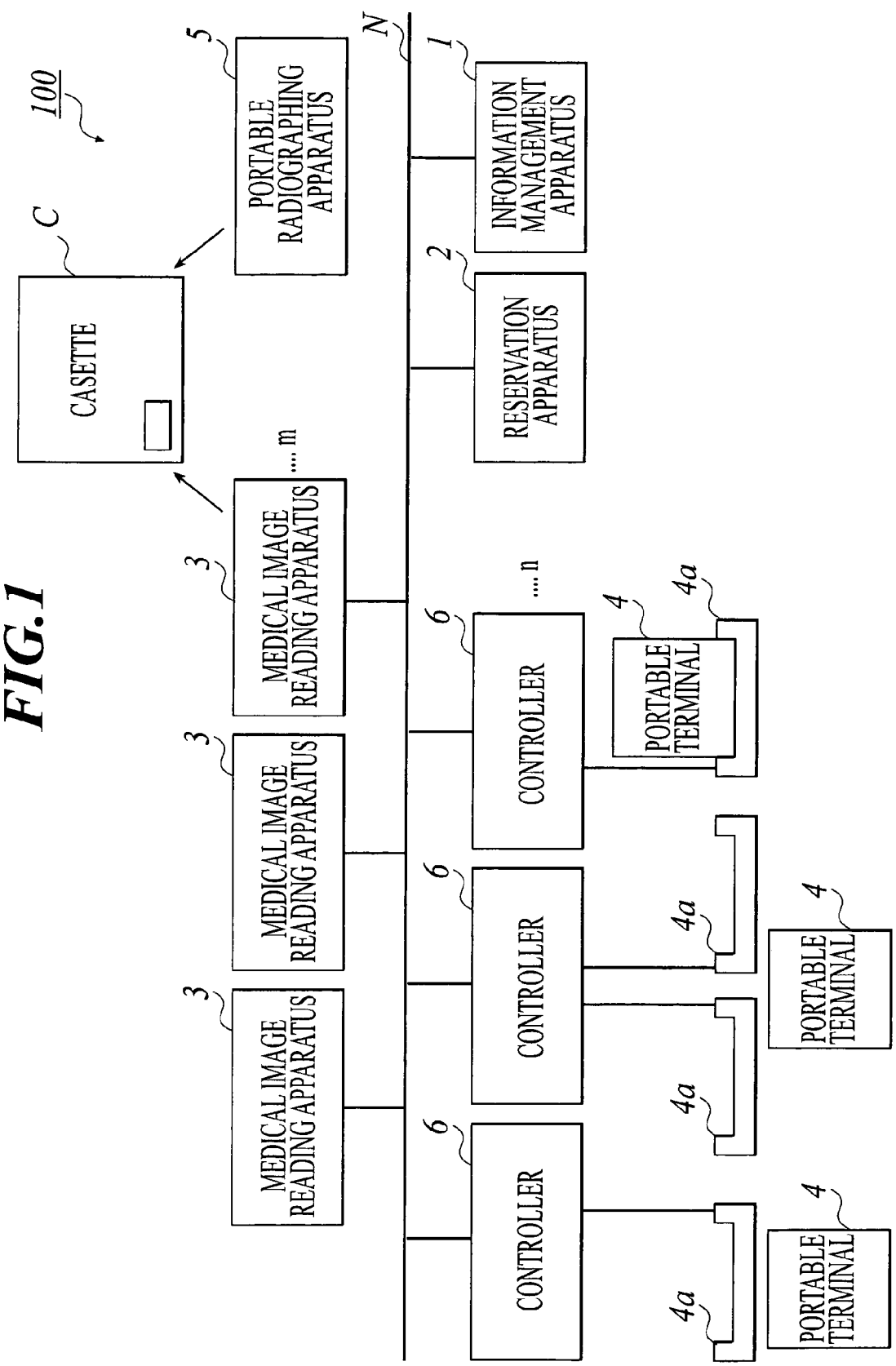
FIG. 1 is a view showing a conceptual structure of a medical image radiographing system 100 in a first embodiment to which the present invention is applied.

First, with reference to FIG. 1, a conceptual structure of a medical image radiogrpahing system 100 will be described. FIG. 1 is a block diagram showing the conceptual structure of the medical image radiographing system 100. As shown in FIG. 1, the medical image radiographing system 100 is placed in hospital facilities and it comprises an information management apparatus 1, a reservation apparatus 2, a medical image reading apparatus 3, a portable terminal 4, a communication terminal 4a, a portable radiographing apparatus 5, a controller 6 and the like. Further, the information management apparatus 1, the reservation apparatus 2, the medical image reading apparatus 3 and the controller 6 are capable of transmitting and receiving data with each other through a network N such as LAN (Local Area Network), WAN (Wide Area Network) or the like, which is built in the hospital facilities.

Further, one or a plurality of communication terminals 4a, which are for transmitting and receiving data with the portable terminal 4, are wiredly connected to one controller 6. The number of the medical image reading apparatus 3 and the controller 6 can be any, for example, 'm' medical image reading apparatuses 3 and 'n' controllers 6 are placed. Each controller 6 is capable of communicating with any one of the 'm' medical image reading apparatuses 3 through the network N, and obtaining medical image data from any medical image reading apparatuses 3.

Further, a plurality of information management apparatuses 1, a plurality of reservation apparatuses 2 and a plurality of portable radiographing apparatuses 5 can also be placed in the hospital facilities. In particular, the portable radiographing apparatus 5 can be placed in a dedicated space placed at each floor in the hospital facilities or each nurse station (illustration is omitted in both the cases).

When the information management apparatus 1 receives radiographing order information transmitted from HIS/RIS or the controller 6, the information management apparatus 1 stores the received radiographing order information.

Here, to the radiographing order information, a flag (hereinafter, it is referred to as a potable designation flag) indicating whether it is radiographing order information for normal radiography or it is radiographing order information for portable radiography performed with the use of the portable radiogrpahing apparatus 5 at a bedside in a hospital room, is added. If the portable designation flag is off, it means that it is radiographing order information for normal radiography. If the portable designation flag is on, it means that it is radiographing order information for portable radiography.

When the information management apparatus 1 receives the radiographing order information with a cassette ID added to, transmitted from the controller 6, the information management apparatus 1 updates the radiographing order information stored into the received radiographing order information with the cassette ID added to. Further, the information management apparatus 1 stores medical image data obtained from the medical image reading apparatus 3.

Here, a structure of the information management apparatus 1 and a structure of the radiographing order information with the cassette ID added to will be described in detail later.

The reservation apparatus 2 is respectively placed in an examination reception room and each consultation room, and is an input terminal for a doctor or the like to input radiographing order information regarding radiography. A PC terminal placed in each consultation room and an examination reception room corresponds to the reservation apparatus 2. The reservation apparatus 2 transmits the inputted radiographing order information to HIS/RIS.

The medical image reading apparatus 3 reads medical image data from a cassette C set in a reading unit, which is not illustrated. Here, the cassette C includes an imaging plate in which a photostimulable phosphor layer is formed, or comprises such imaging plate (illustration is omitted in both the cases). The medical image reading apparatus 3 makes the photostimulable phosphor layer of the imaging plate emit fluorescence corresponding to accumulated radiation energy, photoelectrically converts the emitted fluorescence and outputs medical image data.

Further, on the surface of the cassette C, that is, the imaging plate and/or the cassette, a barcode unique to the cassette C is labeled as a cassette ID. Here, the cassette ID of the cassette C is not limited to the barcode as long as it is possible to identify the cassette C. For example, an IC chip in which cassette ID is recorded may be used.

The portable terminal 4 is a portable-type information terminal carried at the time of radiography, by a radiographic operator who operates the portable radiographing apparatus 5 or the like. The portable terminal 4 is placed in a predetermined place in a hospital room that holds patients, for example, a nurse station or the like, along with the communication terminal 4a, the cassette C, the portable radiographing apparatus 5 and the like.

When the portable terminal 4 is set in the communication terminal 4a and becomes capable of transmitting and receiving data with the controller 6, which is connected to the communication terminal 4a, the portable terminal 4 transmits and receives data with the controller 6.

The portable terminal 4 is, for example, a PDA (Personal Digital Assistant). However, the portable terminal may be a laptop PC or the like. Further, the communication terminal 4a is, for example, a Cradle.

Here, a structure of the portable terminal 4 will be described in detail later.

The portable radiographing apparatus 5 is a radiographing apparatus capable of traveling among hospital rooms and beds, and performs radiography (X-ray) with the use of the cassette C at a bedside in each hospital room.

The controller 6 transmits and receives data with the portable terminal 4 through one or a plurality of communication terminals 4a, which are connected thereto wiredly.

Further, the controller 6 downloads radiographing order information from the information management apparatus 1 and transmits the downloaded radiographing order information to each portable terminal 4 through the communication terminal 4a connected wiredly thereto. Further, at the controller 6, it is possible to input and edit the radiographing order information, and the controller 6 uploads radiographing order information to the information management apparatus 1, the radiographing order information after the input/edit or the radiographing order information with the cassette ID added to transmitted from the portable terminal 4.

Further, the controller 6 is capable of displaying medical image data obtained from the medical image reading apparatus 3, and thereby it is possible for a radiographic operator to easily confirm a result of radiography. In this case, preferably the medical image reading apparatus 3 and the controller 6 are placed together in the same room or at the same floor, and thereby it is possible for a radiographic operator to confirm the result of radiography without traveling among rooms or floors.

Here, a structure of the controller 6 will be described in detail later.

In other words, when the radiographing order information inputted from HIS/RIS or the controller 6 is transmitted to the portable terminal 4 in the hospital room, a radiographic operator refers to the radiographing order information displayed on a display screen of the portable terminal 4 which he/she carries, and confirms a patient to be radiographed at a bedside of a hospital room and a size/number of sheet of the cassette C necessary for the radiography. Next, the radiographic operator conveys the cassette C of the confirmed size/number of sheet, the portable terminal 4 and the portable radiographing apparatus 5 to the bedside of the hospital room that holds the patient to be radiographed. Then, the radiographic operator records correspondence between the radiographing order information and the cassette C (that is, the cassette ID) in the portable terminal 4 at each time of radiography, and after the completion of all the radiography, the radiographic operator sets the portable terminal 4 in the communication terminal 4a. At this time, the radiographing order information with the cassette ID added to is automatically uploaded to the information management apparatus 1 from the portable terminal 4.

Here, the portable terminal 4 verifies a patient. ID inputted by the radiographic operator and a patient ID included in the radiographing order information, and displays a result of the verification on a display screen of a display unit 43. Here, the portable terminal 4 may have a function to notify the result by sound. Further, preferably, the patient ID is inputted to the portable terminal 4 with the use of a barcode. In this case, since operation of confirming a patient to be radiographed is performed not by eye observation of the radiographic operator but by a computer, reliability can be increased.

Figure 2:
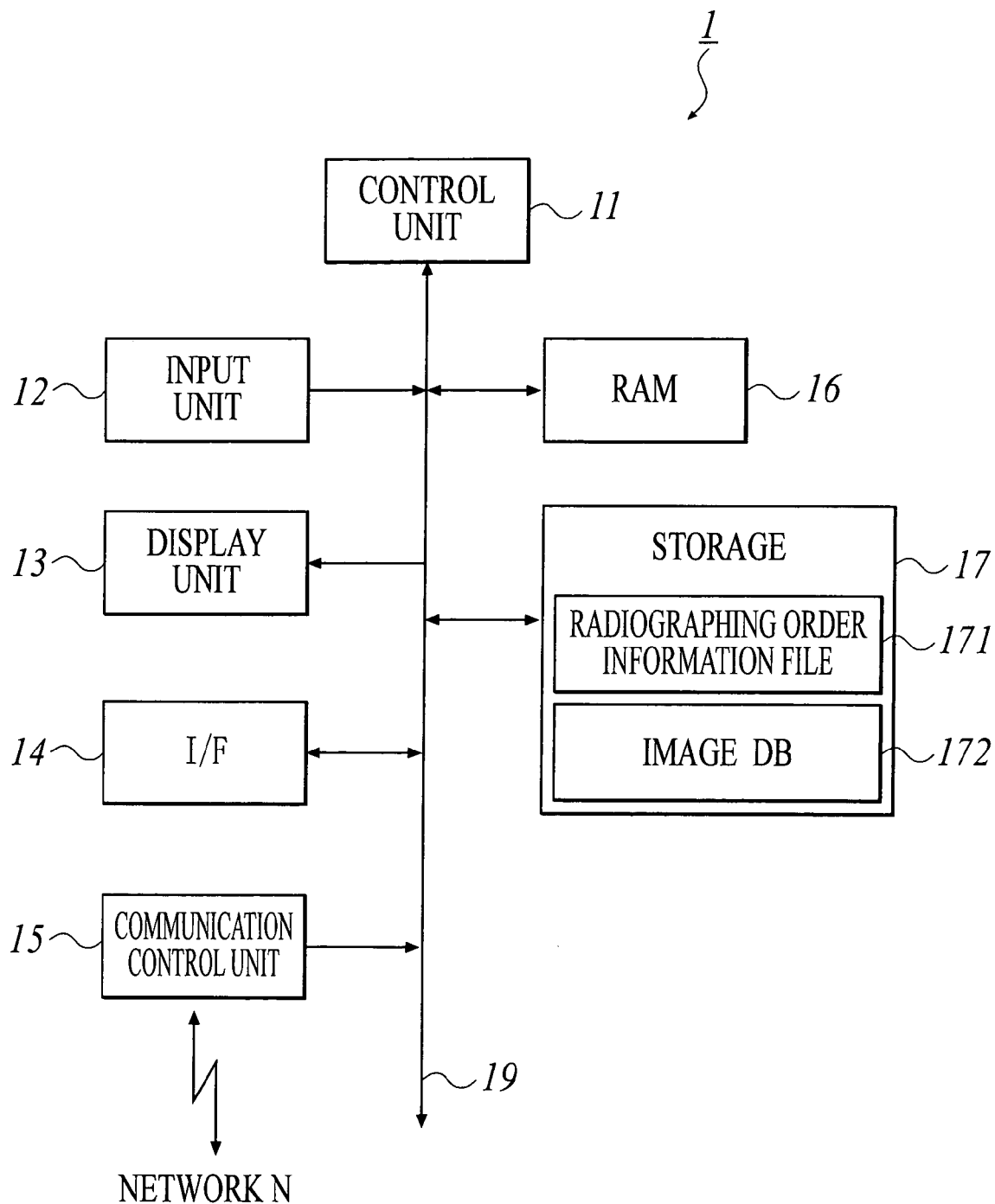
FIG. 2 is a block diagram showing an internal structure of an information management apparatus 1.
Figure 3:
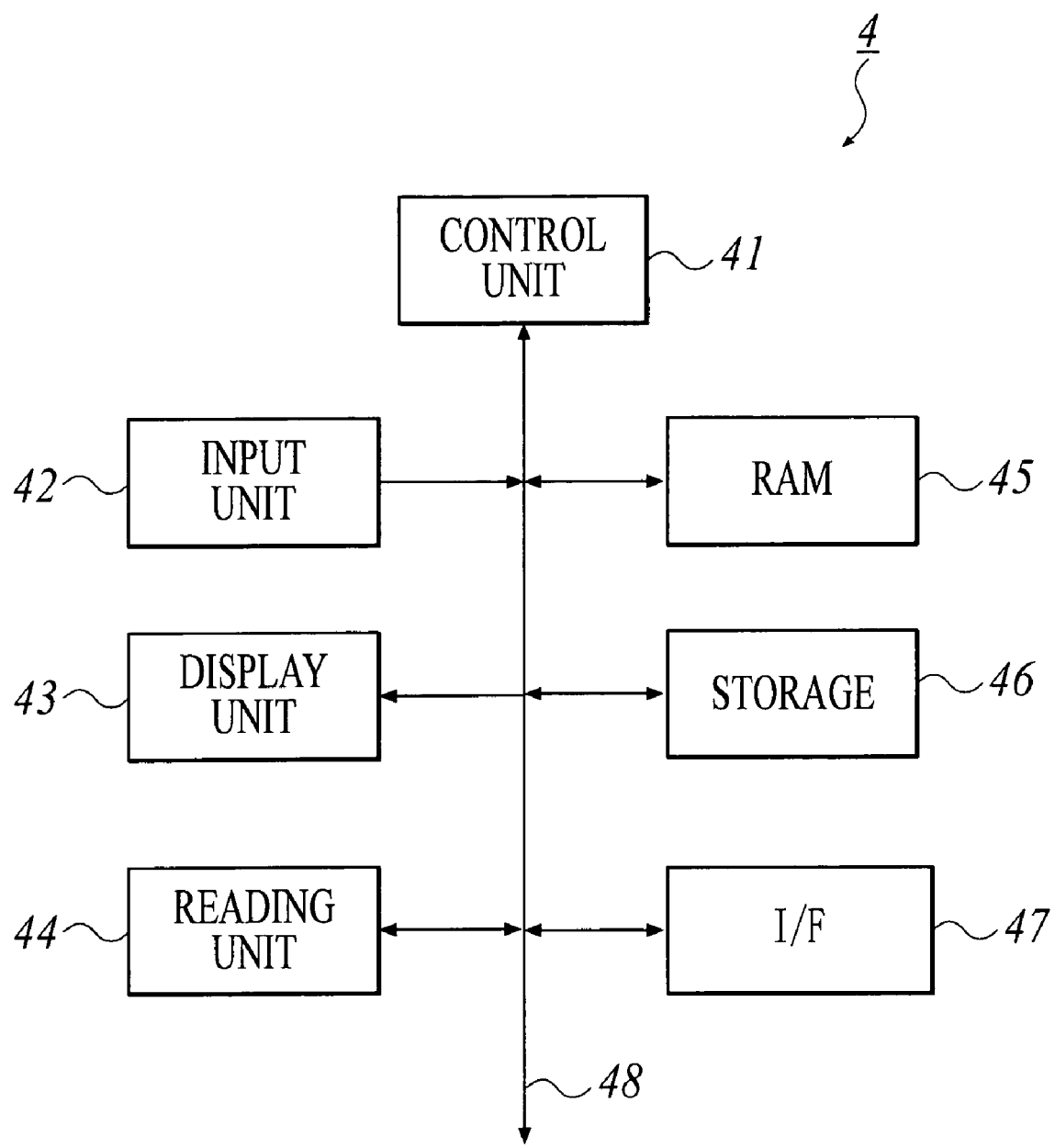
FIG. 3 is a block diagram showing an internal structure of a portable terminal 4 shown in FIG. 1.
Figure 4:
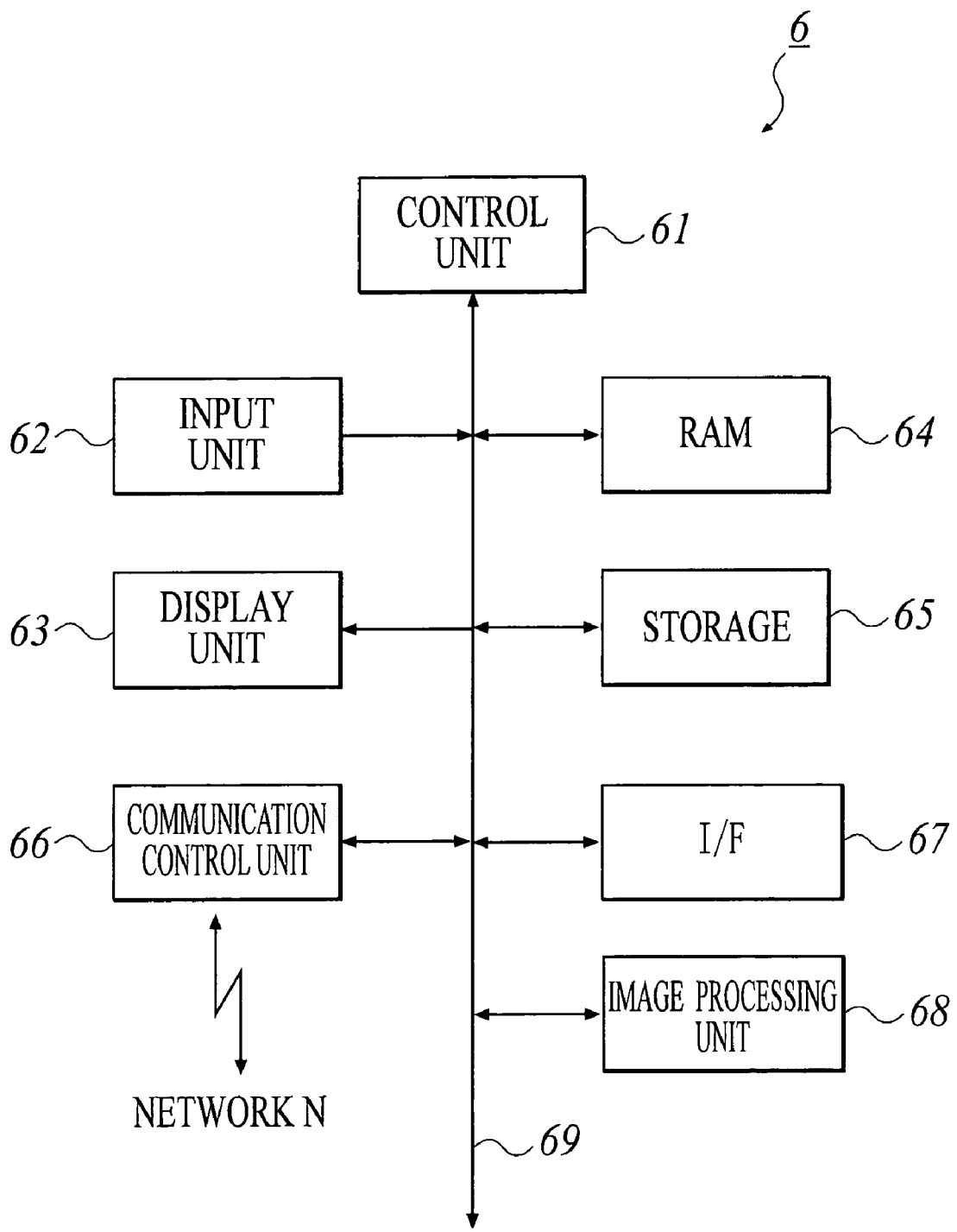
FIG. 4 is a block diagram showing an internal structure of a controller 6 shown in FIG. 1.

Next, with reference to FIGS. 2, 3 and 4, structures of the information management apparatus 1, the portable terminal 4 and the controller 6 will be described in detail. FIG. 2 shows an internal structure of the information management apparatus 1, FIG. 3 shows an internal structure of the portable terminal 4 and FIG. 4 shows an internal structure of the controller 6.

First, the structure of the information management apparatus 1 will be described.

As shown in FIG. 2, the information management apparatus 1 comprises a control unit 11, an input unit 12, a display unit 13, an I/F 14, a communication control unit 15, a RAM 16, a storage unit 17 and the like. Each unit is connected through a bus 19.

The control unit 11 loads various types of programs stored in the storage unit 17 to execute. In particular, the control unit 11 loads a program for executing information process illustrated as a flowchart in FIG. 5, which will be described in detail later, to execute.

When the control unit 11 receives the radiographing order information transmitted from HIS/RIS or the controller 6, the control unit 11 records the received radiographing order information in a radiographing order information file 171. Further, when the control unit 11 receives the radiographing order information with the cassette ID added to transmitted from the controller 6, the control unit 11 updates the radiographing order information recorded in the radiographing order information file 171 to the received radiographing order information with the cassette ID added to. Further, the control unit 11 stores the medical image data obtained from the medical image reading apparatus 3 in an image DB (Data Base) 172.

The input unit 12 is composed of a keyboard comprising cursor keys, numeric input keys, various types of function keys and the like, and a pointing device such as a mouse or the like (illustration of these components is omitted), and the input unit 12 outputs an instruction signal inputted through keyboard operation on the keyboard or mouse operation to the control unit 11. Further, the input unit 12 may comprise a touch panel placed on a display screen of the display unit 13 to output an instruction signal input through the touch panel to the control unit 11.

The display unit 13 comprises a display screen such as a LCD (Liquid Crystal Display), which is not illustrated, a CRT (Cathode Ray Tube) or the like, and displays data for various types of display according to a display control signal by the control unit 11.

The I/F 14 is an interface for transmitting and receiving data with the controller 6 and for receiving the radiographing order information from HIS/RIS.

The communication control unit 15 is composed of a LAN board, a router, a TA (Terminal Adapter) or the like (illustration of these components is omitted), and the communication control unit 15 controls communication performed among each apparatus connected to the network N.

The RAM (Random Access Memory) 16 develops therein various types of programs loaded from the storage unit 17 by the control unit 11 as executable. Further, the RAM 16 temporarily stores various types of data generated at the time of program execution by the control unit 11.

The storage unit 17 is, for example, composed of a nonvolatile semiconductor memory where data can be written/erased such as HDD (Hard Disc Drive) or the like, and the storage unit 17 stores various types of programs and various types of data. In particular, the storage unit 17 stores a program for executing communication process illustrated as a flowchart in FIG. 5, which will be described in detail later.

The storage unit 17 comprises the radiographing order information file 171 and the image DB 172. The radiographing order information file 171 records therein the radiographing order information inputted from HIS/RIS or the controller 6. The image DB 172 stores medical image data processed by the controller 6 with patient ID information correspondingly.

Here, the storage unit 17 may comprise a recording medium (illustration is omitted) in which various types of programs and various types of data are stored. The recording medium is placed on the storage unit either fixedly or detachably, and is a nonvolatile memory composed of a magnetic recording medium, an optical recording medium or a semiconductor memory.

Next, the structure of the portable terminal 4 will be described.

As shown in FIG. 3, the portable terminal 4 comprises a control unit 41, an input unit 42, a display unit 43, a reading unit 44, a RAM 45, a storage unit 46, an I/F 47 and the like, and each unit is connected through a bus 48.

The control unit 41 loads various types of programs stored in the storage unit 46 to execute. In particular, the control unit 41 loads a program to execute an information process illustrated in a flowchart of FIG. 6, which will be described in detail later, to execute.

When set to a mode for radiography, preferably, the control unit 41 controls the input unit 42, which will be described later, so as to make only a jog dial operable. Thereby, it is possible to avoid a situation where a radiographic operator makes an input by mistake during the radiography.

When the portable terminal 4 is set in the communication terminal 4a, the control unit 41 transmits the radiographing order information with the cassette ID added to, to the controller 6 through the communication terminal 4a, and erase the data which already has been transmitted.

When a radiographic operator carries the portable terminal 4, that is, in the case that the portable terminal 4 has not yet been re-set in the communication terminal 4a for transmitting and receiving data with the controller 6 ever since the radiographic operator once carries the portable terminal 4, the control unit 41 refuses to register the identical cassette ID.

The input unit 42 is composed of cursor keys, numeric input keys, various types of function keys and the like (illustration of these components is omitted), and the input unit 42 outputs an instruction signal inputted through key operation on the various types of keys to the control unit 41.

The input unit 42 comprises a jog dial. The input unit 42 outputs an instruction signal to the control unit 41, the instruction signal for scrolling (moving) various types of display parts on the display screen of the display unit 43 by dial operation on the jog dial. Further, the input unit 42 outputs an input (determination) instruction to the control unit 41, the input instruction on the scrolled display parts by pushing the jog dial.

Here, the input unit 42 may comprise a touch panel placed on the display screen of the display unit 43. In this case, the input unit 42 outputs an instruction signal inputted at the touch panel to the control unit 41.

The display unit 43 comprises a display screen such as an LCD, which is not illustrated, or the like, and displays data for various types of displays according to a display control signal by the control unit 41. In particular, the display unit 43 displays the radiographing order information obtained from the controller 6 through the communication terminal 4a.

The reading unit 44 comprises a barcode reader, which is not illustrated, detachably, and outputs barcode information such as the cassette ID or the like read by the barcode reader, to the control unit 41.

The RAM 45 develops therein the various types of programs loaded from the storage unit 46 by the control unit 41 as executable and stores them. Further, The RAM 45 temporarily stores various types of data generated when the control unit 41 executes programs, for example, the radiographing order information, the cassette ID read by the reading unit 44 and the like.

The storage unit 46 is composed of a nonvolatile semiconductor memory such as HDD or the like, and stores the various types of programs and the various types of data. In particular, the storage unit 46 stores a program for executing a communication process illustrated in the flowchart of FIG. 6, which will be described in detail later.

The storage unit 46 may comprise a recording medium (illustration is omitted) in which the various types of programs and the various types of data are stored. The recording medium is placed either fixedly or detachably with the storage unit 46, and is nonvolatile memory composed of a magnetic recording medium, an optical recording medium or a semiconductor memory.

The I/F 47 is an interface supporting RS-232C, IrDA (Infrared Data Association) and the like for transmitting and receiving data with the control unit 6 through the communication terminal 4a.

Here, the communication terminal 4a is wiredly connected to one controller 6, and it comprises a communication control unit, which is not illustrated, for controlling on transmitting and receiving data with the portable terminal 4 set in a slot, which is not illustrated.

Next, the structure of the controller 6 will be described.

As shown in FIG. 4, the controller 6 comprises a control unit 61, an input unit 62, a display unit 63, a communication control unit 64, a RAM 65, a storage unit 66, an I/F 67 and an image processing unit 68. Each unit is connected through a bus 69.

The control unit 61 loads various types of programs stored in the storage unit 65 to execute. In particular, the control unit 61 loads programs for executing a communication process and an image process illustrated in each flowchart of FIG. 7 and FIG. 8, which will be described in detail later, to execute.

With respect to the medical image data obtained from the medical image reading apparatus 3, the control unit 61 selects a process pattern (including a frequency process, a gradation process, a rotation process, a magnifying/reducing process and the like) according to a radiographing condition such as a radiographic part written in the radiographing order information regarding the medical image data, and the control unit 61 makes the image processing unit 68 perform an image process (including a compression/expansion process) based on the process pattern.

The control unit 61 stores the medical image data on which the image processing unit 68 performs the image process in the image DB 172, with the radiographing order information correspondingly. Here, process pattern information according to the radiographing condition is stored in the storage unit 65.

The input unit 62 is composed of a keyboard comprising cursor keys, numeric input keys, various types of function keys and the like, and a pointing device such as a mouse (illustration of these components is omitted), and the input unit 62 outputs an instruction signal inputted by key operation on the keyboard or mouse operation to the control unit 61. Further, the input unit 62 may comprise a touch panel placed on a display screen of the display unit 63, and output an instruction signal input at the touch panel to the control unit 61.

The display unit 63 comprises a display screen such as an LCD, a CRT, which are not illustrated, or the like, and displays data for various types of displays according to a display control signal from the control unit 61.

The RAM 64 develops therein the various types of programs loaded from the storage unit 65 by the control unit 61 as executable, and stores them. Further, the RAM 64 temporarily stores various types of data generated when the control unit 61 executes programs.

The storage unit 65 is composed of a nonvolatile semiconductor memory such as HDD or the like, and stores the various types of programs and the various types of data. In particular, the storage unit 65 stores programs for executing the communication process and the image process illustrated in each flowchart of FIG. 7 and FIG. 8, which will be described in detail later. Then, the storage unit 65 stores a plurality of process patterns for performing the image process according to the radiographing condition.

The storage unit 65 may comprise a recording medium (illustration is omitted) in which the various types of programs and the various types of data are stored. The recording medium is placed either fixedly or detachably with the storage unit 65, and is nonvolatile memory composed of a magnetic recoding medium, an optical recording medium or a semiconductor memory.

The communication control unit 66 is composed of a LAN board, a router, a TA or the like (illustration of these items is omitted), and controls communication among each apparatus connected to the network N.

The I/F 67 is an interface supporting RS-232C, IrDA and the like for transmitting and receiving data with the portable terminal 5 through the communication terminal 4a.

The image processing unit 68 performs the image process (including the compression/expansion process) on the medical image data obtained from the medical image reading apparatus 3 based on a processing pattern selected according to the radiographing condition written in the radiographing order information regarding the medical image data.

Next, with reference to FIGS. 5 to 8, operation of the information management apparatus 1, the portable terminal 4 and the controller 6 will be described.

Figure 5:
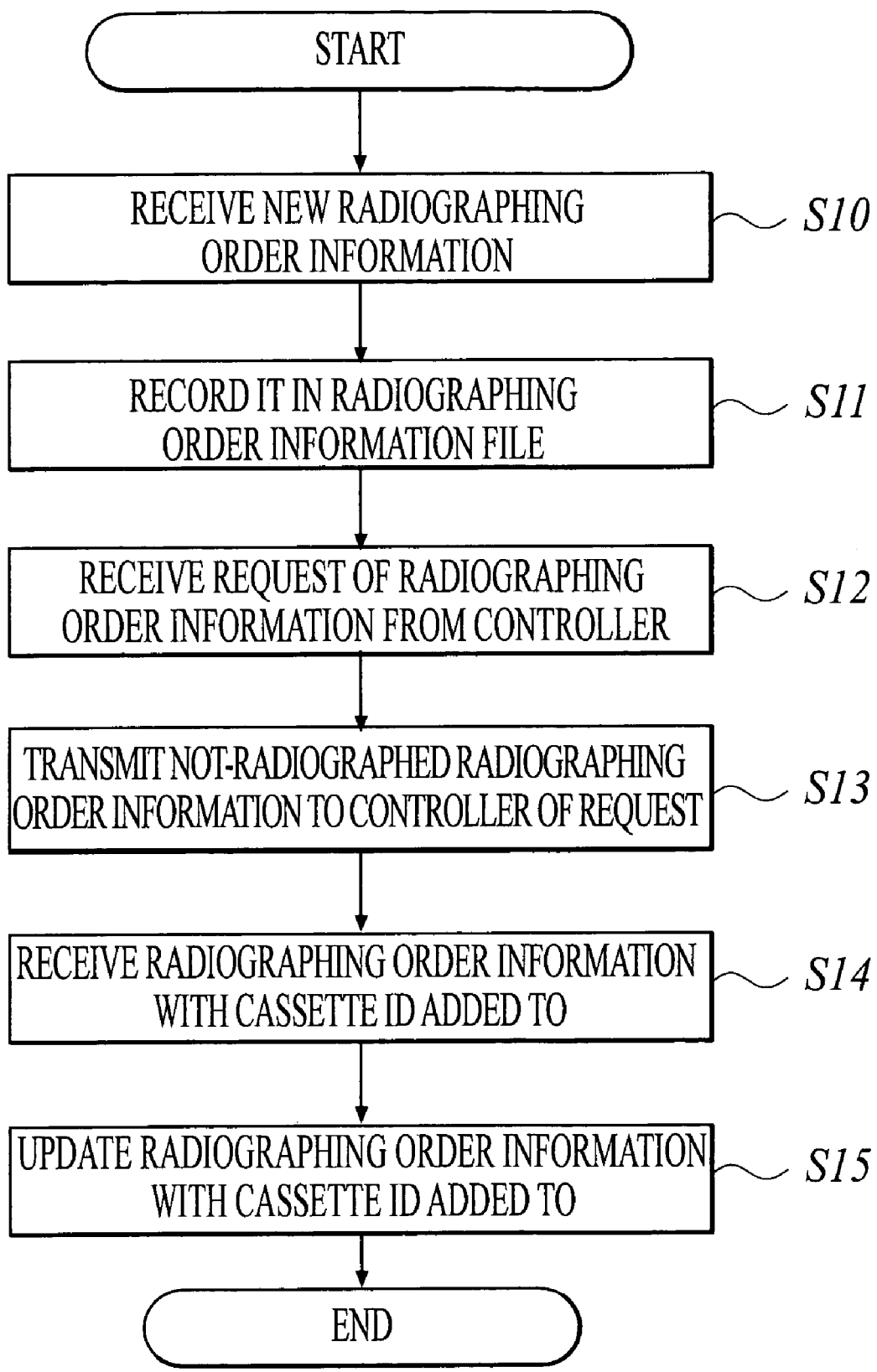
FIG. 5 is a flowchart illustrating an information process executed by the information management apparatus 1 shown in FIG. 1.
Figure 6:
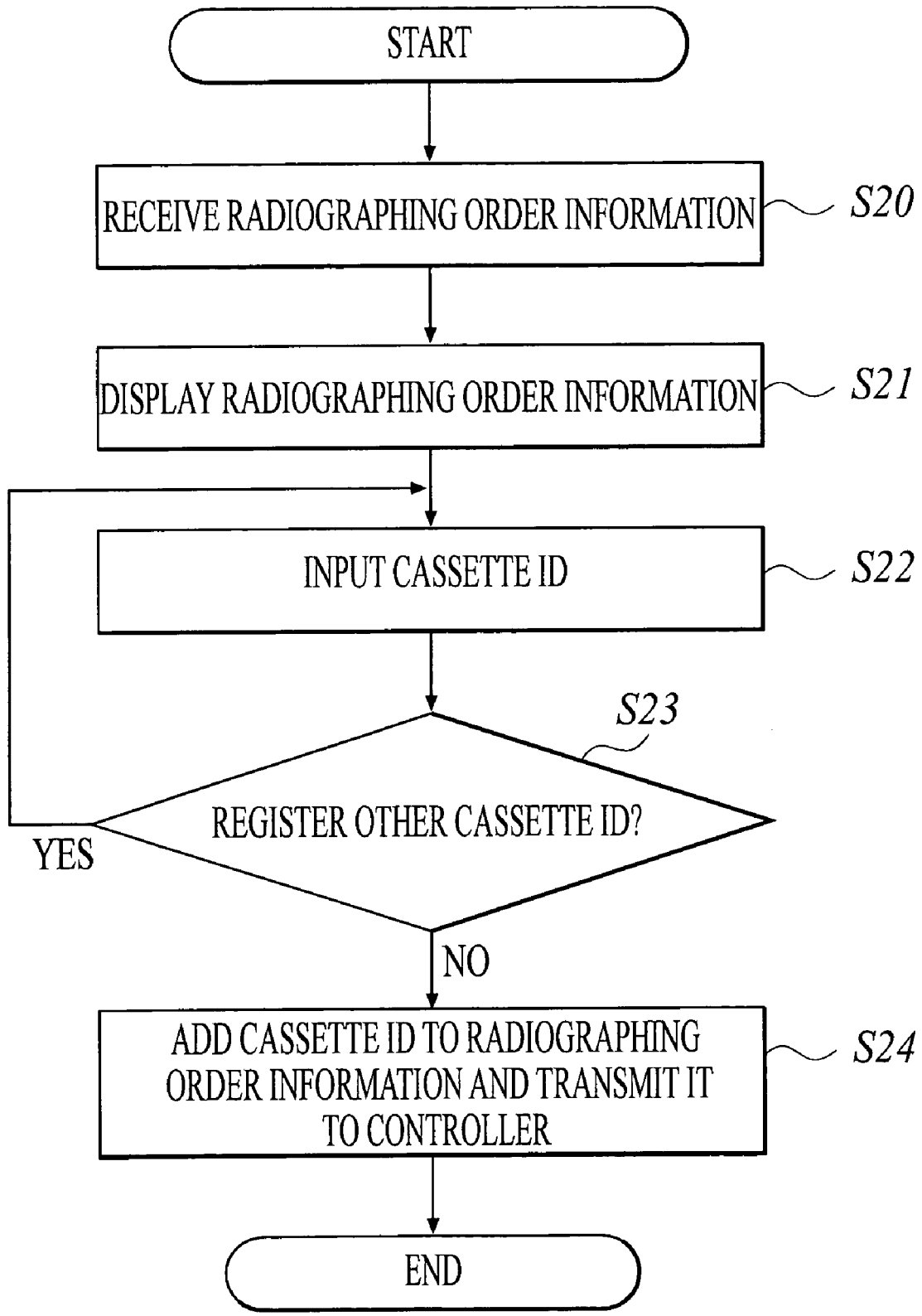
FIG. 6 is a flowchart illustrating a communication process executed by the portable terminal 4 shown in FIG. 1.

FIG. 5 is a flowchart illustrating an information process executed by the information management apparatus 1, FIG. 6 is a flowchart illustrating a communication process executed by the portable terminal 4 and FIGS. 7 and 8 are flowcharts illustrating a communication process and an image process executed by the controller 6, respectively.

First, with reference to FIG. 5, operation regarding the information process by the information management apparatus 1 will be described.

When the control unit 11 receives new radiographing order information from HIS/RIS or the controller 6 (Step 10), the control unit 11 records the new radiographing order information in the radiographing order information file 171 (Step S11).

When the control unit 11 receives a signal instructing to request radiographing order information from the controller 6, the control unit 11 selects radiographing order information of which radiography has not yet been performed (hereinafter, it is referred to as not-performed radiographing order information) among the radiographing order information stored in the radiographing order information file 171, and transmits the selected radiographing order information to the controller 6 that has originally requested the radiographing order information (Step S13). Here, the not-performed radiographing order information means radiographing order information without the cassette ID added to.

Here, if a plurality of controllers 6 are active and all the plurality of controllers 6 request radiographing order information, the control unit 11 transmits the not-performed radiographing order information to all the plurality of controllers 6. The request of radiographing order information is made by inputting at either B1 shown in FIG. 10A or at B3 shown in FIG. 10B according to selection.

In Step S13, when the controller 6 requests the control unit 11 to transmit radiographing order information for portable radiography in particular, the control unit 11 selects not-performed radiographing order information for portable radiography by referring to a portable designation flag which has been added to the radiographing order information, among the radiographing order information stored in the radiographing order information file 171, and then the control unit 11 transmits the selected radiographing order information to the controller 6 that has originally requested the radiographing order information.

When the control unit 11 receives from the controller 6, the radiographing order information with the cassette ID added to (Step S14), the control unit 11 updates the corresponding radiographing order information to the received radiographing order information with the cassette ID added to (Step S15). Further, when the controller 6 transmits radiographing order information for updating, to the control unit 11, the control unit 11 updates the corresponding radiographing order information to the radiographing order information for updating.

Next, with reference to FIG. 6, operation regarding the communication process by the portable terminal 4 will be described.

When the portable terminal 4 receives the radiographing order information from the controller 6 while being set in the communication terminal 4a (Step S20), the control unit 41 displays the received radiographing order information on the display screen of the display unit 43 (Step S21).

After Step S21, when a radiographic operator carries the portable terminal 4 and inputs an instruction at the input unit 42, the control unit 41 functions according to the instruction. For example, after the radiographic operator confirms that patient information (patient name, patient ID) of the radiographing order information displayed on the display unit 43 corresponds to patient information of a patient to be radiographed, and then the radiographic operator inputs an instruction to read cassette ID of the cassette C to be used for each radiographing condition displayed at A4 of FIG. 9B, the control unit 41 directly reads the cassette ID (barcode information) of each cassette C from each cassette C through the barcode reader of the reading unit 44 (Step S22, Step S23; Yes). For example, at A5 of FIG. 9B, displayed are a radiographic part "CHEST ETC OBLIQUE" as the radiographing order information, and a cassette ID (barcode information) "04000108022016" of the cassette to be used for radiographing the radiographic part, the cassette ID read in Step S23. By repeating the above-mentioned operation according to counts of radiography, one-to-one correspondence between a radiographing condition and a cassette is set.

In this case, preferably, the radiographic operator does not perform the reading of cassette IDs of all the radiographing panels to be used for radiography, but performs the reading of a cassette ID of each radiography at each time. Thereby, it is possible to avoid a situation where a radiography panel is used for radiography whose radiographing condition is different from the one corresponding to the radiography panel.

After the completion of reading all the cassette IDs to be used for radiography, that is, the control unit 41 completes the registration of radiography panels and radiography (Step S23; No), when the portable terminal 4 is set in the communication terminal 4a so that the portable terminal could become capable of transmitting and receiving data with the controller 6, the control unit 41 adds the cassette ID to the radiographing order information of which radiography has been performed and transmits it to the controller 6, and the control unit 41 erases the data which has been transmitted (Step S24).

Here, FIG. 9A and FIG. 9B show display examples of the radiographing order information to be displayed on the display screen of the display unit 43 with respect to Step S21. FIG. 9A is a display example of a patient name and a patient ID, and FIG. 9B is a display example of a radiographing condition designated to each patient.

In a screen 431 shown in FIG. 9A, patient names and patient IDs are displayed in a list form at A1. In particular, a patient name "ICHIRO YAMADA" and his patient ID "0001", and a patient name "TARO SAKURA" and his patient ID "12345" are displayed in a list form at A2. A radiographic operator operates a dial of the jog dial of the input unit 42 for selecting a patient name and a patient ID of one patient from these two patients, and further pushes the jog dial while the patient is being selected. Thereby, radiographing order information regarding the selected patient is displayed. For example, a screen 432 shown in FIG. 9B is to show the case that the radiographic operator selects the patient name "ICHIRO YAMADA" and the patient ID "0001" at A2 according to dial operation on the jog dial, the radiographic operator pushes the jog dial while the patient is being selected, and then a radiographing condition regarding a patient of the patient name "ICHIRO YAMADA" and the patient ID "0001" are displayed on the display screen of the display unit 43.

In the screen 432 shown in FIG. 9B, the patient name "ICHIRO YAMADA", the patient ID "0001" and the like are displayed at A3, and the radiographing condition "CHEST ETC OBLIQUE", the cassette ID "04000108022016" (see A5), a radiographing condition "CHEST ETC APICAL" (see A6) are displayed in a list form at A4. A4 can be scrolled by dial operation on the jog dial of the input unit 42, and thereby it is possible to display a radiographing condition which could not all at once be displayed at A4.

Next, operation of the controller 6 will be described.

First, with reference to FIG. 7, operation regarding the communication process of the controller 6 will be described.

Figure 10A:
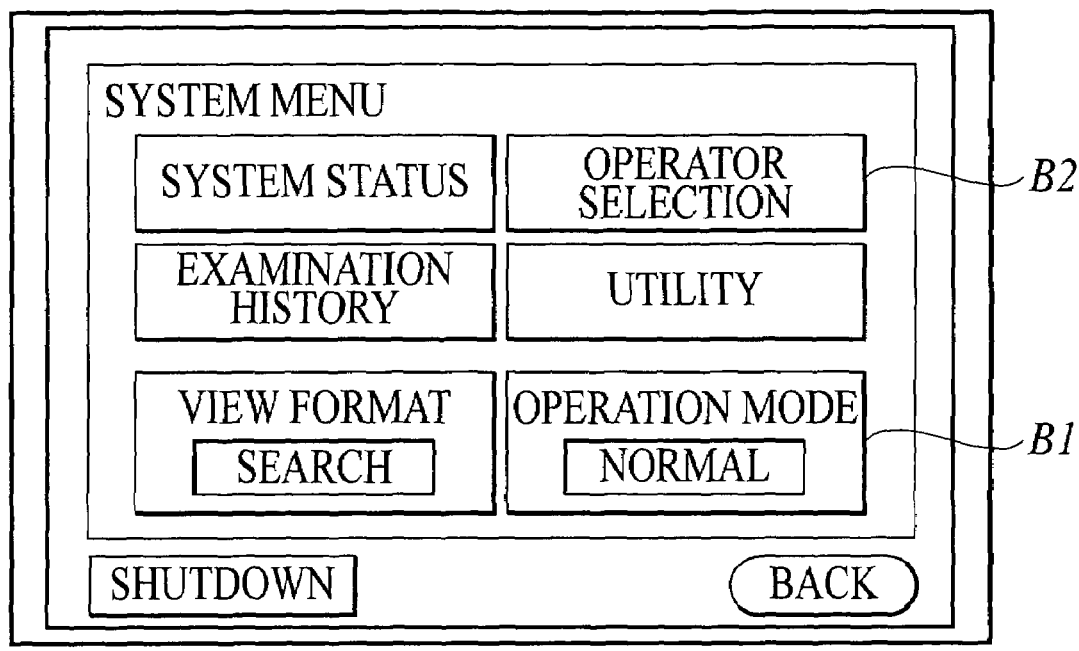
FIG. 10A is one example of a screen displayed on a display screen of the controller 6 shown in FIG. 1, the screen to designate the display of not-radiographed radiographing order information for normal radiography.
Figure 10B:
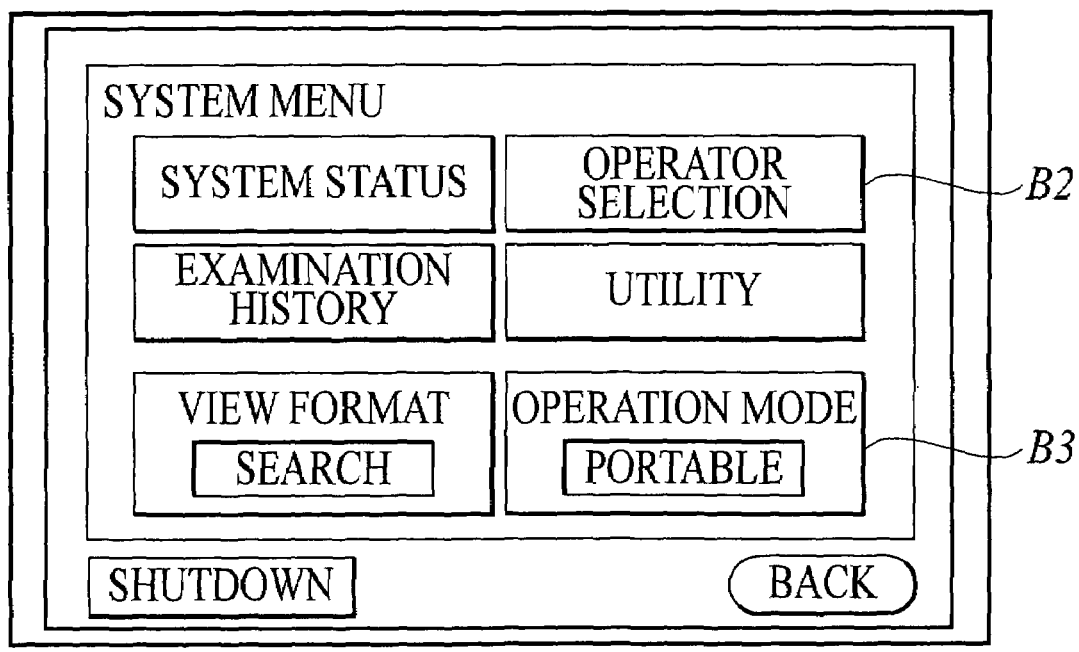
FIG. 10B is one example of a screen displayed on the display screen of the controller 6 shown in FIG. 1, the screen to designate the display of not-radiographed radiographing order information for portable radiography.

When the radiographing order information is to be downloaded from the information management apparatus 1 or to be newly inputted, the control unit 61 displays either a screen 631 shown in FIG. 10A or a screen 632 shown in FIG. 10B on the display screen of the display unit 63 according to an instruction inputted by a radiographic operator. In this case, when an instruction of requesting all the not-performed radiographing order information for normal radiography is inputted at the input unit 62, the screen 631 shown in FIG. 10A is displayed on the display screen of the display unit 63. When an instruction of requesting all the not-performed radiographing order information for portable radiography is inputted at the input unit 62, the screen 632 shown in FIG. 10B is displayed on the display screen of the display unit 63.

Here, in either the screen 631 of FIG. 10A or the screen 632 of FIG. 10B, when an input button "OPERATOR SELECTION" displayed at B2 is key-inputted with the mouse or with the touch panel of the input unit 62, list information of radiographic operators is transmitted from the information management apparatus 1 to make it possible to select a radiographic operator to perform radiography from the list.

When an input button "OPERATION MODE (NORMAL)" displayed at B2 at the screen 631 of FIG. 10A is key-inputted with the mouse or the touch panel of the input unit 62, the control unit 61 downloads all the not-performed radiographing order information for normal radiography from the information management apparatus 1. When an input button "OPERATION MODE (PORTABLE)" displayed at B2 at the screen 632 of FIG. 10B is key-inputted with the mouse or the touch panel of the input unit 62, the control unit 61 downloads all the not-performed radiographing order information for portable radiography from the information management apparatus 1 (Step S30).

In the case of portable radiography, if the not-performed radiographing order information for portable radiography is not registered in the information management apparatus 1, a radiographic operator either inputs new radiographing order information for potable radiography or key-inputs the input button "OPERATION MODE (NORMAL)" displayed at B1 with the mouse or the touch panel of the input unit 62 in order to download all the not-performed radiographing order information for normal radiography from the information management apparatus 1 for changing some of the not-performed radiographing order information for normal radiography to ones for portable radiography according to need. In other words, when the radiographing order information for normal radiography is downloaded, the radiographic operator, according to need, selects some of the radiographing order information to be changed to ones for portable radiography among the downloaded radiographing order information for normal radiography, then a portable designation flag of the selected radiographing order information is set to "ON", and after returning to the screen for selecting "OPERATION MODE (PORTABLE)" (see B2), the operation re-enters the portable mode.

The control unit 61 transmits the radiographing order information for portable radiography to the portable terminal 4 set in the communication terminal 4a through the communication terminal 4a (Step S31). The control unit 61 also uploads newly inputted radiographing order information or radiographing order information which has been changed from one for normal radiography to one for portable radiography, among the radiographing order information for portable radiography to the information management apparatus 1.

When the control unit 61 receives the radiographing order information with the cassette ID added to, that is, already-performed radiographing order information from the portable terminal 4 set in the communication terminal 4a, which is connected to the controller (Step S32), the control unit 61 uploads the received radiographing order information with the cassette ID added to, to the information management apparatus 1 (Step S33).

Here, with reference to FIGS. 11, 12 and 13, input operation at the time of newly inputting radiographing order information for portable radiography will be described. Hereafter, the displaying of display screens of display unit 62 shown in FIGS. 11, 12 and 13, and later-described FIG. 14 to 18 are controlled by the control unit 61.

First, when an instruction to register new radiographing order information is inputted, for example, a screen 633 shown in FIG. 11 is displayed on the display screen of the display unit 63 for inputting patient information such as patient name, patient ID and the like regarding the new radiographing order information at the input unit 62.

Here, at B4, input keys are displayed and a key input on the displayed input keys is made with the mouse or the touch panel of the input unit 62. Further, it is possible to make a key input with the keyboard comprised in the input unit 62. At B5, each input part of patient ID, name (roman letter, kana, kanji) is displayed. At B6, when the input button "OPERATOR SELECTION" displayed at B2 of FIG. 10A and FIG. 10B is key-inputted with the mouse or the touch panel of the input unit 62, a name of the inputted operator is displayed.

Figure 12:
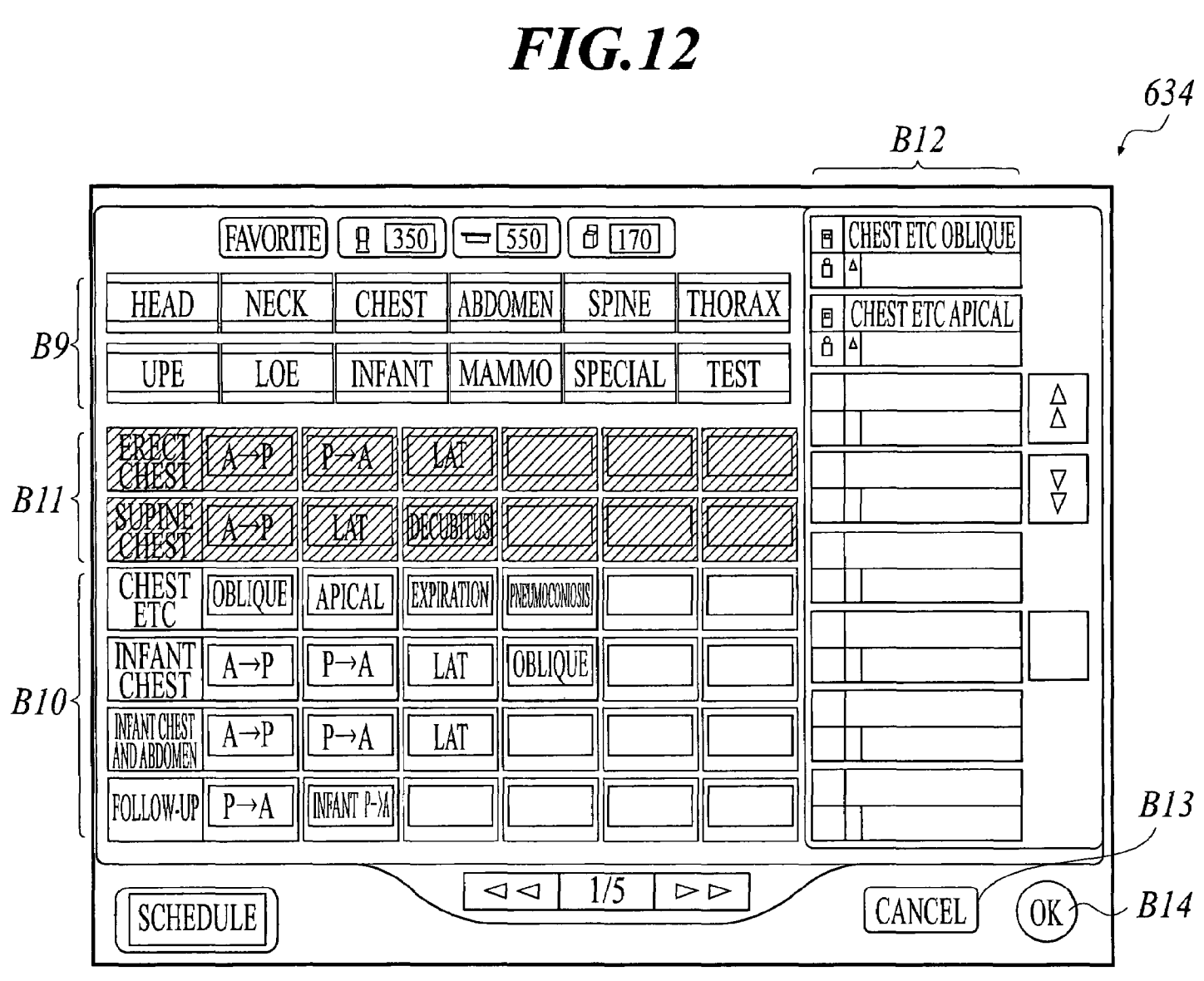

When B8 is key-inputted with the mouse or the touch panel of the input unit 62, for example, a screen 634 shown in FIG. 12 is displayed on the display screen of the display unit 63 for setting a radiographing condition according to the patient name and the patient ID displayed at B5. At B9, selection buttons of large classification items of a radiographing condition, "HEAD, NECK, . . . , TEST", are displayed and when any one of the large classification items of the radiographing condition is key-inputted with the mouse or the touch panel of the input unit 62, classification items of more detailed radiographing condition "ERECT ERECT (A→P, . . . , LAT), . . . , FOLLOW-UP (P→A, INFANT PA)" corresponding to the inputted classification item (for example, "CHEST") are displayed at B10 and B11. In the classification items of B10, for example, if "CHEST ETC OBLIQUE" and "CHEST ETC APICAL" are key-inputted, the key-inputted radiographing conditions are displayed as a list at B12.

Here, the radiographing conditions displayed with mesh at B11 are radiographing conditions of which portable radiography is impossible to perform. Thereby, it is possible to make it obvious to show whether the radiographing order information to be inputted is for portable radiography or for normal radiography. As a result, it is possible to avoid a situation where an input of a radiographing condition of which portable radiography is impossible to perform is made when a radiographic operator inputs radiographing order information for portable radiography.

Here, in the present embodiment, described is the case that the items of the radiographing conditions of which portable radiography is impossible to perform are displayed with mesh. However, the method is not limited to such description. For example, while both the items of radiographing condition of which portable radiography is possible to perform and of which portable radiography is impossible to perform are displayed together in the same display form, when an item of the radiographing condition of which portable radiography is impossible to perform is key-inputted by mistake, warning which indicates that it is not possible to input may be provided with sound or images.

When B14 is key-inputted with the mouse or the touch panel of the input unit 62, for example, a screen 635 shown in FIG. 13A is displayed on the display screen of the display unit 63, where patient names, patient IDs and the like of the inputted radiographing condition are displayed as a list. At B15, displayed is information of the registered patients, that is, the two patients, who are a patient having a patient ID "0001" and a patient name "ICHIRO YAMADA", and a patient having a patient ID "12345" and a patient name "TARO SAKURA".

Figure 13B:
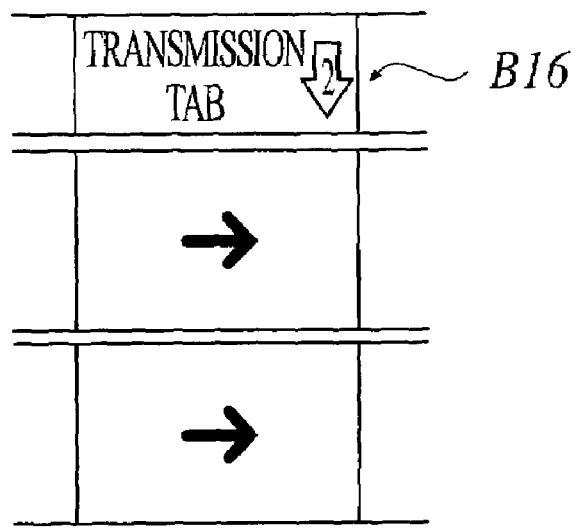
Figure 13C:
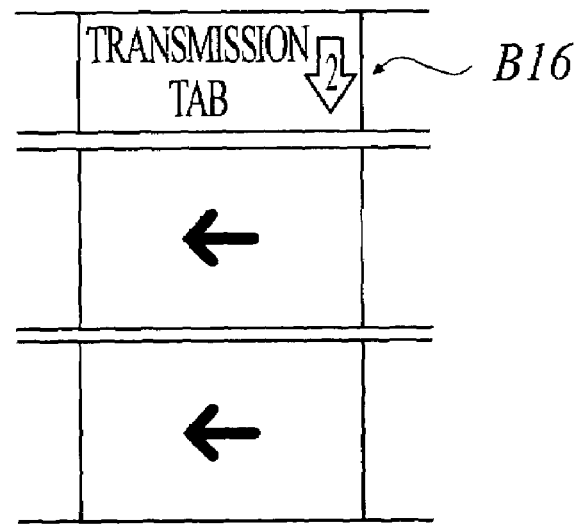

Here, if the radiographing order information of each patient displayed as a list as seen at B15 is transmitted from the controller 6 to the portable terminal 4, for example, as shown in FIG. 13B, a mark "→" (a rightward arrow) indicating that the transmission from the controller 6 to the portable terminal 4 has been done is displayed at B16. Further, if the radiographing order information transmitted to the portable terminal 4 is transmitted back along with the cassette ID (that is, as the already-performed radiographing order information) from the portable terminal 4, as shown in FIG. 13C, a mark "←" (a leftward arrow) indicating that the transmission from the portable terminal 4 to the controller 6 has been done is displayed at B16. Here, what is displayed is not limited to the marks "→" or "←", and other marks may be displayed.

Further, when an input button "CANCEL" displayed at B7 in FIG. 11 or B13 in FIG. 12 is key-inputted with the mouse of the touch panel of the input unit 62, the control unit 61 cancels new radiographing order information being inputted. Further, even after the completion of inputting new radiographing order information, an input button "DELETE" displayed at B17 in FIG. 13 is key-inputted with the mouse of the touch panel of the input unit 62, the control unit 61 cancels the input-completed radiographing order information.

Further, with reference to FIG. 14 and FIG. 15, input operation at the time of newly inputting radiographing order information for normal radiography and input operation at the time of changing radiographing order information to one for portable radiography will be described.

First, when an instruction to register new radiographing order information is inputted, a screen identical to the screen 633 for newly inputting radiographing order information for portable radiography (see FIG. 11) is displayed on the display screen of the display unit 63 for inputting patient information such as a patient name, a patient ID and the like regarding the new radiographing order information at the input unit 62. Next, as a screen for newly inputting radiographing order information for normal radiography, a screen approximately identical to the screen 634 for newly inputting radiographing order information for portable radiography (see FIG. 12) is displayed on the display screen of the display unit 63. FIG. 14 shows this screen. Here, since normal radiography can be performed at all the radiographing conditions, B18 of a screen 636 shown in FIG. 14 is displayed without mesh unlike the screen shown in FIG. 12.

When B20 is key-inputted with the mouse of the touch panel of the input unit 62, for example, a screen 637 shown in FIG. 15 is displayed on the display screen of the display unit 63, where patient names, patient IDs and the like of the inputted radiographing condition are displayed as a list.

At B21, ON/OFF of portable designation is displayed per each patient. One displayed with "ON" is radiographing order information which has been changed to one for portable radiography (that is, its portable designation flag is "ON"), and one displayed with "OFF" is radiographing order information for normal radiography (that is, its portable designation flag is "OFF"). Then, when an input key "PORTABLE DESIGNATION" displayed at B22 is key-inputted with the mouse or the touch panel of the input unit 62, ON/OFF of a portable designation flag of the radiographing order information is switched at each time of a key input. Data of the portable designation flag is included in radiographing order information.

Further, when an input button "EXTRACTION CONDITION" displayed at B23 is key-inputted with the mouse or the touch panel of the input unit 62, only the radiographing order information corresponding to the inputted extraction condition is extracted or sorted.

Figure 14:
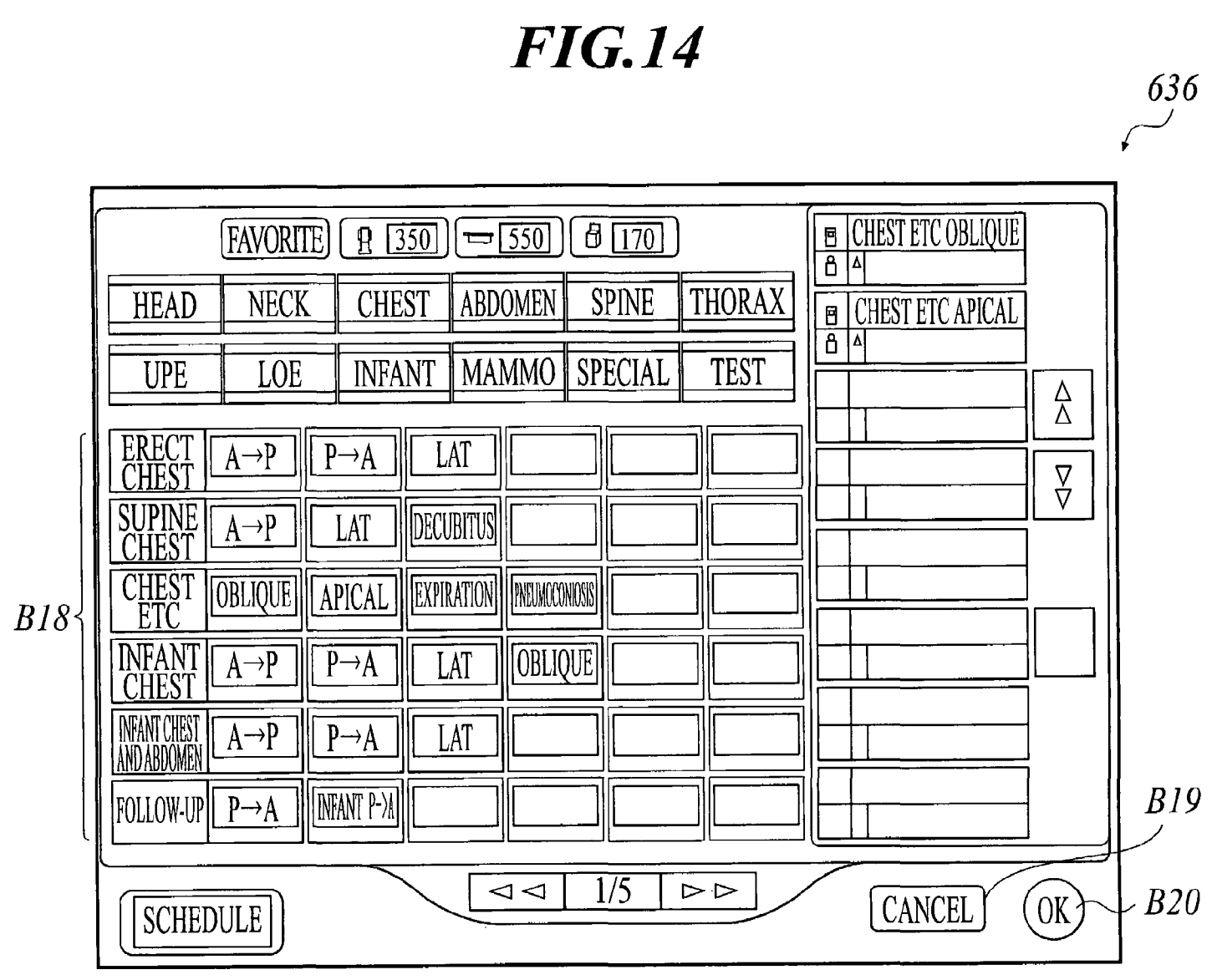

Further, when an input button "CANCEL" displayed at B19 in FIG. 14 is key-inputted with the mouse or the touch panel of the input unit 62, the control unit 61 cancels the new radiographing order information being inputted. Further, even after the completion of inputting the new radiographing order information, if an input button "DELETE" displayed at B24 in FIG. 15 is key-inputted with the mouse or the touch panel of the input unit 62, the control unit 61 cancels the input-completed radiographing order information.

Further, in the controller 6, even if radiographing order information to be newly inputted is either for portable radiography or for normal radiography, at each time of completing the input of new radiographing order information to one patient, for example, a screen 638 shown in FIG. 16 is displayed on the display screen of the display unit 63. When an input button "READY FOR NEXT RADIOGRAPHING ORDER INPUT" displayed at B25 is key-inputted with the mouse or the touch panel of the input unit 62, the control unit 61 allows the system to accept an input of new radiographing order information. Further, when an input button "COMPLETE" displayed at B26 is key-inputted with the mouse or the touch panel of the input unit 62, the control unit 61 completes series of the above-mentioned downloading and newly inputting radiographing order information.

Here, instead of inputting radiographing order information per one patient at once, a structure where the process returns to the screen shown 633 in FIG. 11 by inputting a key "NEW/SEARCH" next to B22 shown in FIG. 15 for registering additionally is also acceptable. In this case, the screen 638 shown in FIG. 16 is not necessary to be displayed.

Next, with reference to FIG. 8, operation regarding the image process of the controller 6 will be described.

The control unit 61 obtains medical image data from the medical image reading apparatus 3, the medical image data regarding the radiographing order information which is transmitted and received with the portable terminal 4 (Step S40). In this case, if 'm' medical image reading apparatuses 3 are placed, the control unit 61 requests all the 'm' medical image reading apparatuses 3 to obtain the medical image data.

At this time, the medical image reading apparatus 3 confirms whether medical image data regarding the cassette ID corresponding to each cassette ID transmitted from the controller 6 is stored in a memory (illustration is omitted) or not. If the medical image data having the corresponding cassette ID is stored in the memory, such medical image data is transmitted to the controller that has originally requested the medical image data.

After the image processing unit 68 performs image process, the control unit 61 displays the medical image data obtained in Step S40 along with the radiographing order information on the display screen of the display unit 63 (step S41).

After Step S41, the control unit 61 performs image modification on the medical image data according to an image modification instruction inputted at the input unit 62 (Step S42), and the control unit 61 uploads the modified medical image data along with the radiographing order information to the information management apparatus 1 (Step S43).

Here, with reference to FIG. 17, medical images displayed on the display screen of the display unit 63 of the controller 6 will be described (see the above description of Step S41 and S42 shown in FIG. 8). The medical images to be described here are radiographed by portable radiography. Here, the displaying of the display screen of the display unit 63 shown in FIG. 17 is controlled by the control unit 61.

Figure 17:
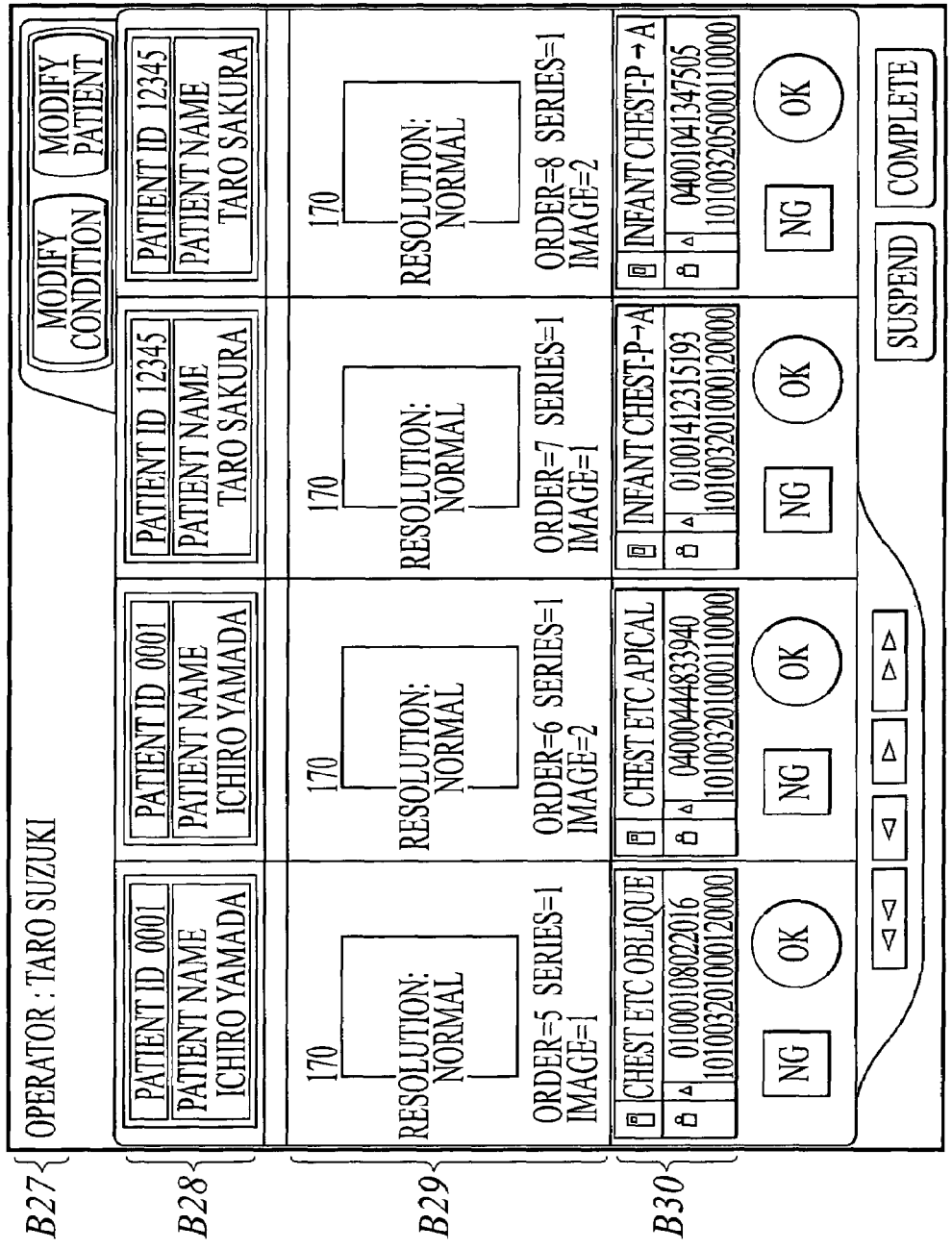
FIG. 17 is one example of an image process screen under a portable mode displayed on the display screen of the controller 6 shown in FIG. 1.

First, when medical image data radiographed at portable radiography is obtained from the medical image reading apparatus 3, for example, a screen 639 shown in FIG. 17 is displayed on the display screen of the display unit 63. In other words, the medical image data radiographed at portable radiography obtained from the medical image reading apparatus 3 is processed by each controller 2, and medical images regarding each of a plurality of radiographing conditions of a plurality of patients, the medical images processed by one portable terminal 4, are displayed in parallel. For example, at B28 to B30, two medical images regarding a patient having a patient name "ICHIRO YAMADA" and a patient ID "0001", and two medical images regarding a patient having a patient name "TARO SAKURA" and a patient ID "12345" are displayed in parallel. Here, a medical image which could not be displayed within one screen can be displayed by scrolling the screen.

Here, patient IDs and patient names are displayed at B28, medical images are displayed at B29, and radiographing conditions, their identification number and cassette ID used for radiography are displayed at B30.

As described above, the medical image radiographing system 100 comprises the information management apparatus 1 for managing radiographing order information and medical image data, the medical image reading apparatus 3 for reading the medical image data from the cassette C, the portable terminal 4 for setting correspondence between the radiographing order information and cassette ID of the cassette C corresponding to each radiographing condition, the portable radiographing apparatus 5 capable of performing (X-ray) radiography at a bedside in a hospital room, and the controller 6 for obtaining the radiographing order information from the information management apparatus 1, for newly inputting radiographing order information, and for obtaining the medical image data from the medical image reading apparatus 3 to display it.

Further, at the time of obtaining the radiographing order information, the controller 6 displays on the display screen of the display unit 63, the screen 631 (the screen shown in FIG. 10A) for downloading or newly inputting radiographing order information for normal radiography, and the screen 632 (the screen shown in FIG. 10B) for downloading or newly inputting radiographing order information for portable radiography.

Further, at the time of newly inputting radiographing order information, the controller 6 displays on the display screen of the display unit 63, the screen 633, 634 or 636 (each screen of FIG. 11, FIG. 12 and FIG. 14) for inputting patient information (a patient name, a patient ID and the like), a radiographing condition and the like, which is approximately identical in both the cases of normal radiography and portable radiography. In particular, in the case of portable radiography, on a radiographing condition of which radiography is impossible to perform, a display method different from the case of normal radiography (for example, displaying with mesh) is applied.

Further, in both the cases of normal radiography and portable radiography, at each time that an input of new radiographing order information is completed per one patient, the controller 6 displays on the display screen of the display unit 63, a common screen for making a radiographic operator confirm the completion.

Therefore, when radiographing order information is to be inputted, in both the cases of normal radiography and portable radiography, it is possible to input patient information and a radiographing condition with approximately the same operation. Thereby, even in the case that the same radiographic operator inputs radiographing order information for both normal radiography and portable radiography all at once, or in the case that an input of radiographing order information is very complicated due to large number of patients, it is easy for the radiographic operator to recognize which content he/she is currently inputting, and thereby it is sufficiently possible to avoid unexpected contingency such as an input mistake or the like.

Here, the description in the first embodiment is an example of a medical image radiographing system and a method for managing a medical image according to the present invention, and thereby the present invention is not limited to such description. With regard to the structure in detail and the operation in detail of the medical image radiographing system 100 in the first embodiment can be changed without departing the gist of the present invention.

For example, in the first embodiment, described is the case that the communication terminal 4a, that is, the portable terminal 4, is capable of transmitting and receiving data with a specific controller 6 to which the communication terminal 4a is connected. However, the present invention is not limited to such described case. The communication terminal 4a, that is, the portable terminal 4, may be capable of transmitting and receiving data with any one of the controllers 6 comprised in the medical image radiographing system 100.

According to the present invention, when radiographing order information is to be inputted, regardless of both the cases of normal radiography with the use of a radiographic-room-use radiographing apparatus, which is fixedly installed in a radiographic room, and portable radiography with the use of a portable radiographing apparatus, it is possible to input radiographing order information by approximately the same input operations. Moreover, even in the case that the same radiographic operator input ones of normal radiography and of portable radiography all at once, or in the case that the input of radiographing order information is very complicated due to the large number of patients, it is easy for a radiographic operator to recognize which content he/she is currently inputting during the whole work flow, and thereby it is sufficiently possible to avoid unexpected contingency such as an input mistake or the like at both normal radiography and portable radiography.

Second Embodiment

In the above-described first embodiment, described is a medical image radiographing system in a state where controllers and portable terminals are connected in the state of 1:1 and one portable terminal directly transmits and receives information with a specific controller, wherein the controller obtains radiographing order information before the start of radiography, the radiographing order information is displayed and inputted under a portable mode, and then the radiographing order information is transmitted to the portable terminal. In a second embodiment, described is a medical image radiographing system in a state where controllers and portable terminals are connected in the state of M:N and one portable terminal transmits and receives information with any one of the controller through a network, wherein the controller receives the radiographing order information from the portable terminal and displays a medical image corresponding to the radiographing order information under a portable mode after the completion of radiography.

Hereinafter, with reference to figures, the second embodiment of the present invention will be described in detail.

First, a structure of the present embodiment will be described.

Figure 19:
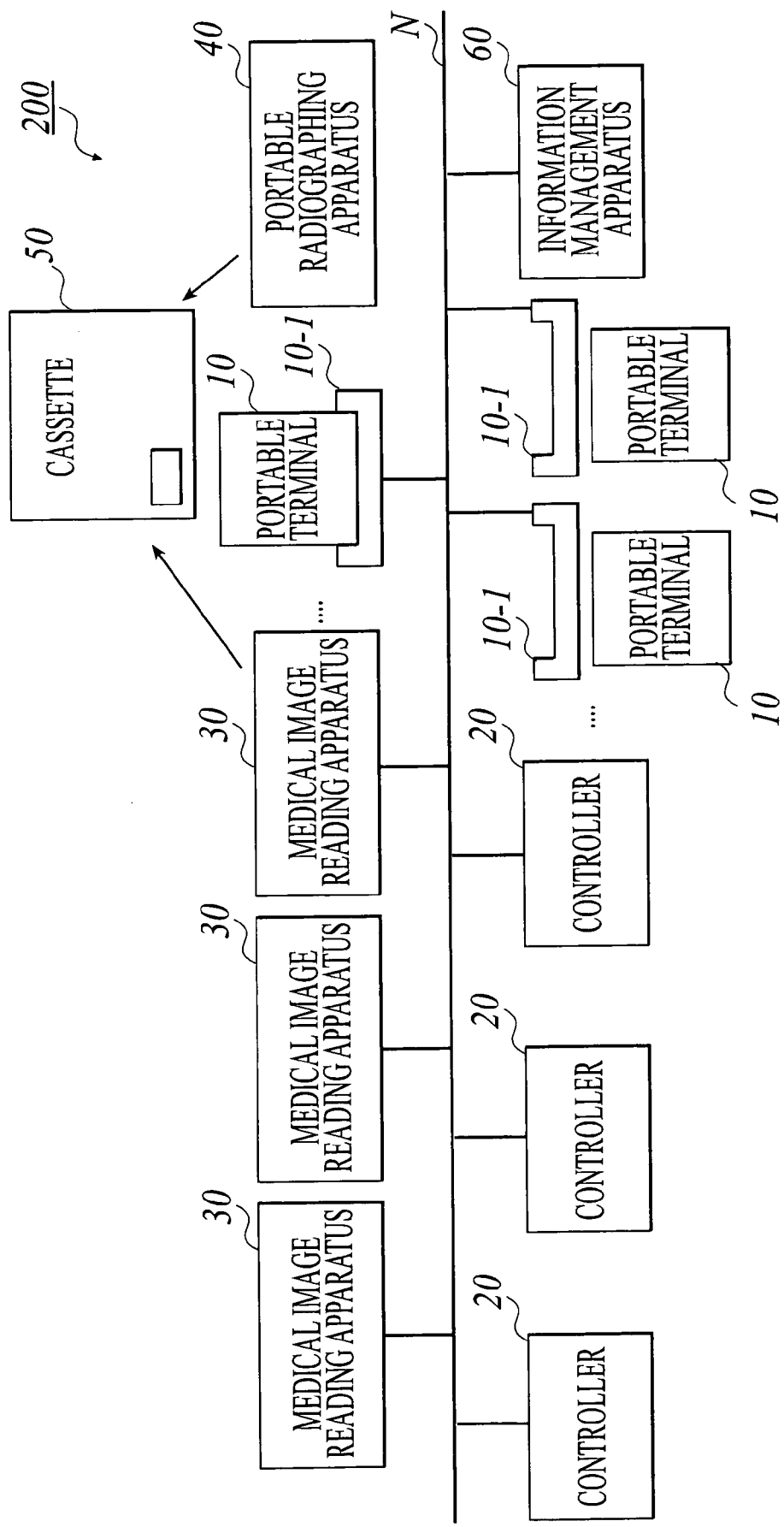
FIG. 19 is a view showing a system structure of a medical image radiographing system 200 in a second embodiment to which the present invention is applied.

FIG. 19 is a conceptual view showing a system structure of a medical image radiographing system 200 according to the present invention. As shown in FIG. 19, the medical image radiographing system 200 comprises a portable terminal 10, a communication terminal 10-1, a controller 20, a medical image reading apparatus 30, a portable radiographing apparatus 40, a cassette 50, an information management apparatus 60 and the like. Further, the communication terminal 10-1, the controller 20, the medical image reading apparatus 30 and the information management apparatus 60 are connected through a network N, and the portable terminal 10 is structured to be connectable to the network N through the communication terminal 10-1.

The portable terminal 10 is a portable-type information terminal device carried by an operator or the like who operates the portable radiographing apparatus 40, and communicates with the controller 20 through the communication terminal 10-1, which will be described later. Further, the portable terminal 10 obtains radiographing order information from the controller 20 and displays it. However, if there is radiographing order information of a plurality of patients, the portable terminal 10 searches for radiographing order information corresponding to a desirable patient ID among the radiographing order information of the plurality of patients and displays it.

The communication terminal 10-1 is connected to each controller 20 through a cable or the like, and controls transmission and reception of data between the portable terminal 10 connected thereto and each controller 20. At this time, when the communication terminal 10-1 detects that the portable terminal 10 is attached thereto, the communication terminal 10-1 transmits a detection signal to each controller 20. Further, the communication terminal 10-1 charges the portable terminal 10 attached thereto.

The controller 20 receives radiographing order information from the information management apparatus 60, and transmits the received radiographing order information to the portable terminal 10 through the communication terminal 10-1. Further, after radiography is performed, the controller 20 receives identification information of the cassette 50 corresponding to the radiographing order information from the portable terminal 10, sets correspondence between the radiographing order information and a medical image based on the identification information of the cassette 50, and manages the medical image. Further, the controller 20 transmits the correspondence between the identification information of the cassette 50 and the radiographing order information to the information management apparatus 60.

Further, if a medical image is radiographed in a normal radiographic room, the controller 20 receives the read medical image and a cassette ID from the medical image reading apparatus and then sets correspondence among the radiographing order, the medical image and the cassette ID.

The medical image reading apparatus 30 is a medical image reading apparatus to read a medical image recorded in the cassette 50. The medical image reading apparatus 30 irradiates excitation light on a photostimulable phosphor sheet of the cassette 50 to emit stimulated light, photoelectrically converts the stimulated light from the sheet to obtain image signals, and A/D-converts the obtained image signals to obtain a medical image. Further, the medical image reading apparatus 30 reads identification information of a cassette accompanied with the cassette 50, and transmits the medical image and the identification information of a cassette corresponding to the medical image to the controller 20.

The portable radiographing apparatus 40 is a traveling-capable medical image radiographing apparatus, and the portable radiographing apparatus 40 radiographs a patient at round visits and records a medical image in the cassette 50, which is detachable to the portable radiographing apparatus 40. The cassette 50 incorporates a photostimulable phosphor sheet which accumulates a part of radiation energy therein. In other words, the cassette 50 accumulates in the above-mentioned photostimulable phosphor sheet, a part of irradiation energy transmitted through a subject placed between a irradiation source and the cassette.

The information management apparatus 60 is a terminal to integrally manage radiographing order information assigned by a doctor. The information management apparatus 60 extracts radiographing order information according to request assignation from the controller 20, and transmits the extracted radiographing order information to the controller 20. Here, as another information management apparatus, a reservation device (not illustrated) for receiving a reservation of radiographing order information may be applied, or an information management system such as HIS (Hospital Information System), RIS (Radiology Information System) or the like may be applied as well.

The network N can take various types of line forms such as LAN (Local Area Network), WAN (Wide Area Network), Internet or the like. Here, if permitted in a medical institution such as a hospital, radio communication or infrared data communication may be used. When radiographing order is transmitted and received, since radiographing order information includes important patient information, preferably radiographing order information is encoded.

Next, each device that can be a principal component in the second invention will be described in detail.

Figure 20:
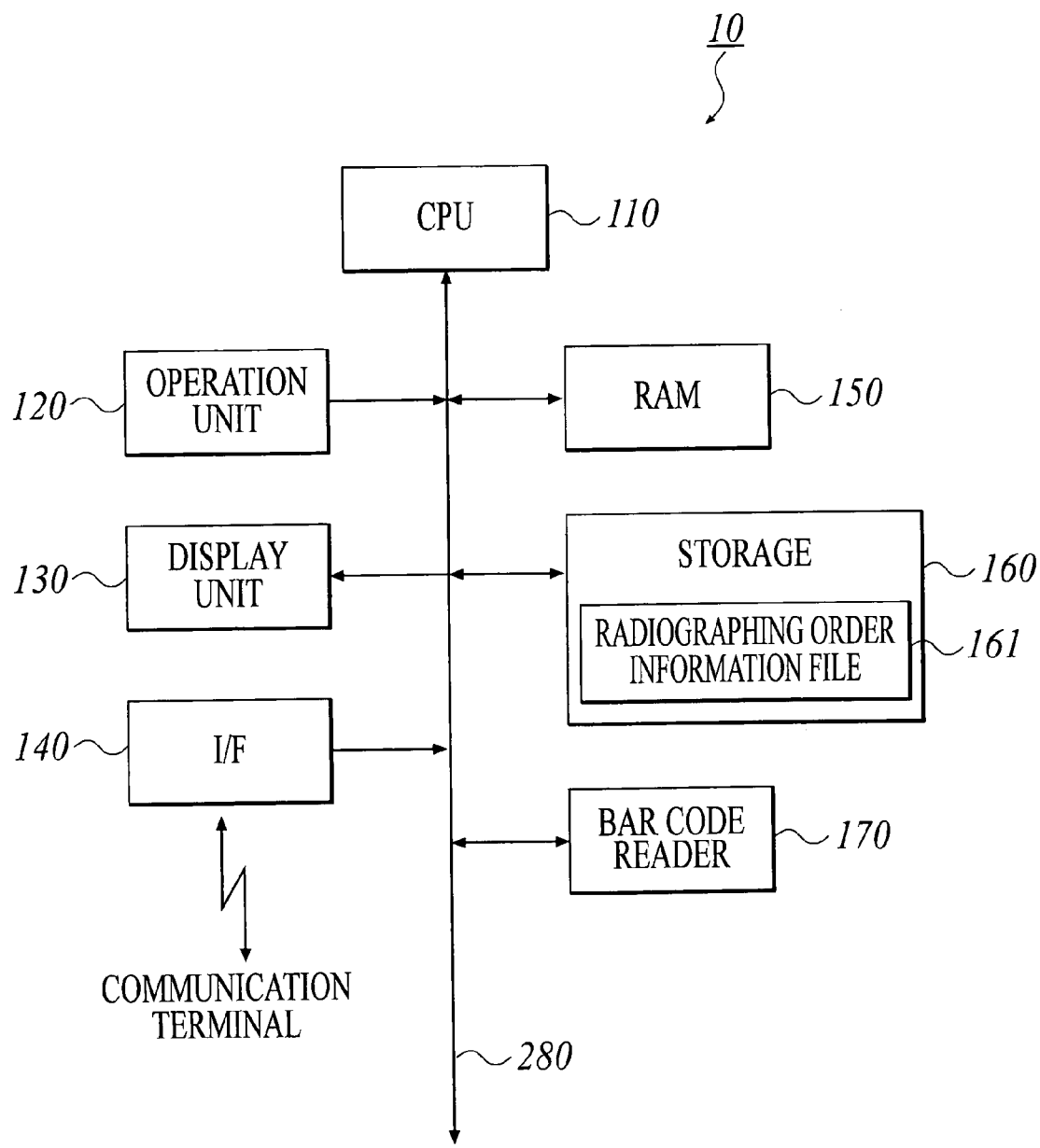
FIG. 20 is a block diagram showing a primary structure of a portable terminal 10 shown in FIG. 19.

FIG. 20 is a block diagram showing a functional structure of the portable terminal 10. As shown in FIG. 20, the portable terminal 10 comprises a CPU 110, an operation unit 120, a display unit 130, an I/F 140 as a communication means, a RAM 150, a storage 160 as a storage means, a barcode reader 170 as an obtaining means, and the like. Each unit is connected through a bus 280.

The CPU (Central Processing Unit) 110 develops a system program and a program designated among various types of application programs stored in the storage 160 into the RAM 15, and according to the developed programs, the CPU 110 integrally controls each unit of the portable terminal 10.

Concretely, the CPU 110 loads a radiography preparation processing program, a radiography start processing program and a radiography completion post processing program from the storage 160, and executes a radiography preparation process (refer to FIG. 24), a radiography start process (refer to FIG. 25) and a radiography completion post process (refer to FIG. 26), which will be described later. Here, details of each process will be described later.

The operation unit 120 comprises cursor keys, numeric keys, various types of function keys, jog dial keys and the like, and outputs a pushed signal corresponding to a pushed key operated by a radiographic operator to the CPU 110. Here, the operation unit 120 may comprise a pointing device such as a touch panel or the like, or another input device according to need.

The display unit 130 is a display means comprising a showing display such as an LCD (Liquid Crystal Display) or the like, and displays various types of information such as radiographing order information, patient ID and the like based on display designation from the CPU 110.

The I/F 140 is an interface to connect the portable terminal 10 and the communication terminal 10-1. When the portable terminal 10 is attached to the communication terminal 10-1, the I/F 140 outputs a detection signal to the CPU 110. Further, the I/F 140 adjusts transfer speed of data and converts a data format-between the portable terminal 10 and the controller 20. In other words, the I/F 140 mediates data exchange between the portable terminal 10 and the controller 20.

For example, the I/F 140 receives radiographing order information from the controller 20. Moreover, the I/F 140 obtains radiographing order information corresponding to identification information of the cassette 50 from the portable terminal 10 after radiography is completed. Here, according to need, a structure where a cell phone such as PHS or the like is connected to the I/F 140 for establishing radio communication so as to transmit and receive data with each other may be used.

The RAM (Random Access Memory) 150 comprises a work memory area for storing the above-mentioned application programs, input designation, input data, processing results and the like.

The storage 160 comprises a storage medium (not illustrated) in which programs and data are stored. This storage medium stores a system program, various types of application programs corresponding to the system program, data processed by the various types of programs and the like. Further, the storage medium is composed of a magnetic storage medium, an optical storage medium or a semiconductor memory, and is to be attached to the storage 160 either fixedly or detachably.

Further, the storage 160 has a radiographing order information file 161 for storing radiographing order information received from the controller 20. With reference to FIG. 21, the radiographing order information file 161 will be described. FIG. 21 is a view showing a data structure example of the radiographing order information file 161. As shown in FIG. 21, the radiographing order information file 161 has items for storing radiographing ID, patient ID, name, sex, age, hospital room, department of request, radiographic part, radiographing apparatus, radiographing count and identification information of the cassette 50 (hereinafter, it is referred to as "cassette ID"). The radiographing order information file 161 stores therein data corresponding to each item at each radiographing order information.

In the item of radiographing ID, stored is an identification code which is uniquely allocated for identifying radiography (for example, 20020101001, 20020101002, 20020101003, . . . ). In the item of patient ID, stored is an identification code which is uniquely allocated for identifying a patient (for example, 10000002, 1000005, . . . ). In the item of name, stored is letter information indicating a name of a patient to be radiographed, in the item of sex, stored is letter information indicating a sex of a patient to be radiographed, in the item of age, stored is numeral information indicating an age of a patient to be radiographed, and in the item of hospital room, stored is letter information indicating a hospital room which is to be a radiography location.

In the item of department of request, stored is letter information indicating a department of request that has requested the corresponding radiography, and in the item of radiographic part, stored is information indicating a radiographic part (for example, SKULL A→P, CHEST R→L, ABDOMEN LAT, . . . ). In the item of radiographing apparatus, stored is letter information indicating a type of a radiographing apparatus to be used for radiography, and in the item of radiographing count, stored is numeral information indicating a count to be radiographed. In the item of cassette ID, stored is a cassette ID (for example, information read from a barcode attached to the cassette 50 or the like) which is uniquely allocated for identifying a cassette used for radiography. Here, data of a cassette ID is not stored at a radiography preparation phase, and the cassette ID read by the barcode reader 170 is stored at the time of radiography at a bedside.

Further, in addition to patient information such as patient ID, name, sex and age, the radiographing order information may further include various types of patient information such as a name of a doctor in charge, warning information which warns infectious disease or the like, existence of drug allergy, existence of pregnancy, additional medical history, necessity of special care such as a wheelchair, a stretcher or the like, a clinical diagnosis name, a secret matter and the like. Further, in addition to the radiography information such as radiographic part, radiographing apparatus and radiographing count, the radiographing order information may further include various types of radiography information, for example, radiographing method (simple radiography, contrast radiography and the like), scheduled radiography date and the like.

The barcode reader 170 is one example of an obtaining means to obtain a cassette ID, and has a scanner, which is an optical reading device. The barcode reader 170 reads a barcode with the use of the scanner, and decodes the read barcode according to a predetermined standard for obtaining information indicated by the barcode. For example, at the time of performing radiography, the barcode reader 170 reads a barcode attached to the cassette 50 in which a medical image is recorded, to obtain a cassette ID. Further, a structure where the barcode reader 170 reads a barcode attached to a bedside of a patient or a part of a patient, and after a patient ID is authenticated, it becomes possible to set the correspondence of the cassette ID to the radiographing order information of the patient, is acceptable. Here, the predetermined standard is, JAN code, UPC code, CODE39, CDE93, CODE128, NW-7, INDUSTRIAL 2 of 5, ITF distribution code or the like.

Figure 22:
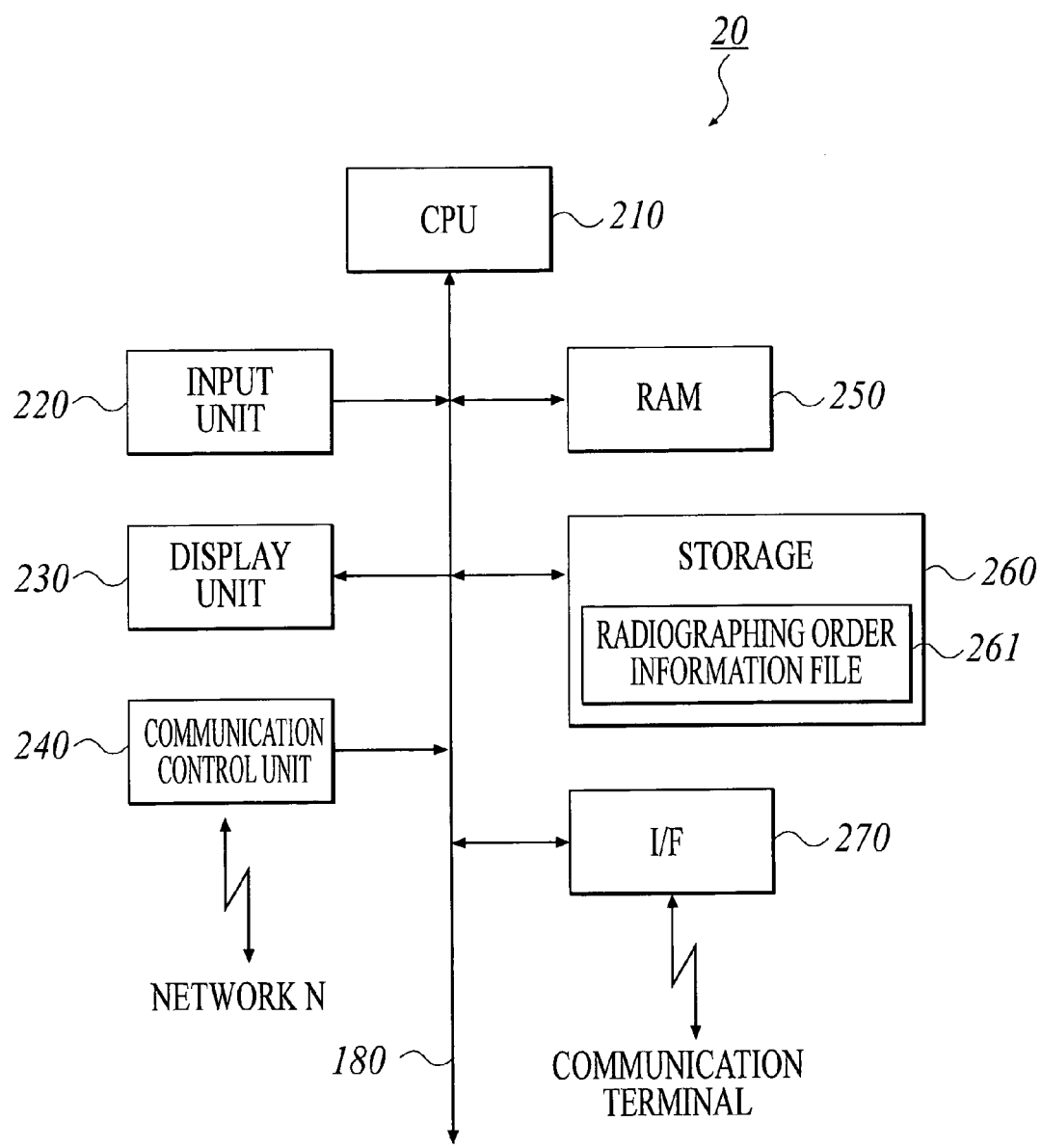
FIG. 22 is a block diagram showing a primary structure of the controller 20 shown in FIG. 19.

FIG. 22 is a block diagram showing a functional structure of the controller 20. As shown in FIG. 22, the controller 20 comprises a CPU 210, an input unit 220, a display unit 230, a communication control unit 240, a RAM 250, a storage 260, an I/F 270 and the like, and each unit is connected through a bus 280.

The CPU 210 loads a system program and various types of control programs stored in the storage 260, develops the loaded program into the RAM 250, and integrally controls operation of each part according to the control programs. Further, the CPU 210 executes various processes according to the programs developed into the RAM 250, and displays the process results on the display 230 as well as temporarily stores them in the RAM 250.

Figure 27:
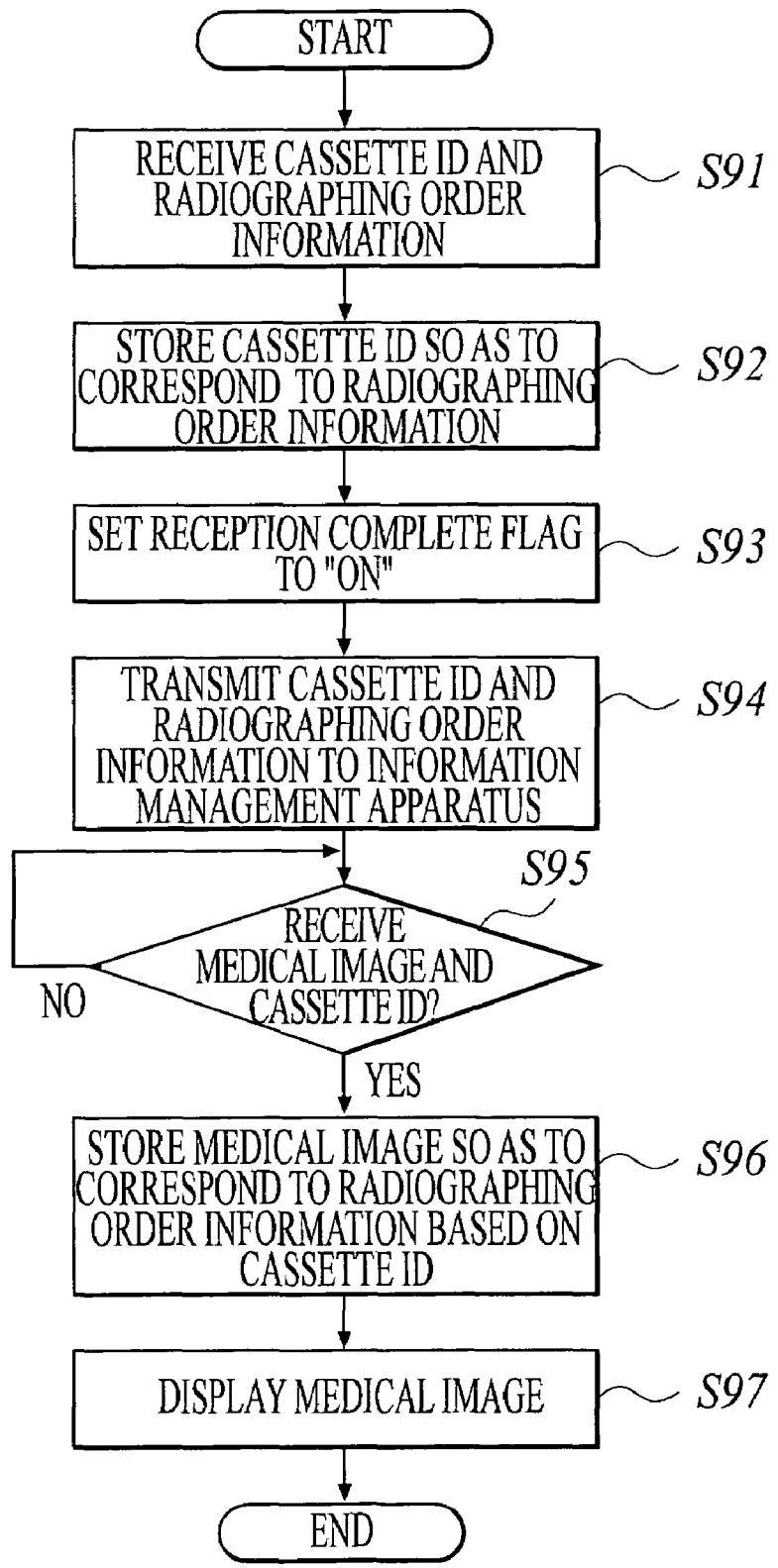
FIG. 27 is a flowchart illustrating a radiography completion post process executed by the CPU 210 of the controller 20.

Concretely, the CPU 210 loads a radiography preparation program and a radiography completion post processing program stored in the storage 260, and executes a radiography preparation process (see FIG. 23) and a radiography completion post process (see FIG. 27).

The input unit 220 comprises a keyboard comprising cursor keys, numeric input keys, various types of function keys and the like, and outputs a pushed signal corresponding to a pushed key on the keyboard to the CPU 210. Here, the input unit 220 may comprise a pointing device such as a mouse, a touch panel or the like, or another input device according to need.

The display unit 230 is composed of an LCD, a CRT (Cathode Ray Tube) or the like, and displays input designation from the input unit 220, data and the like according to designation of a display signal input from the CPU 210.

The communication control unit 240 is composed of a LAN adapter, a TA (Terminal Adapter) or the like, and controls communication among each device connected to the network N through a communication line such as a lease line, an ISDN line or the like.

The RAM 250 forms a storage area for temporarily storing the system program, which can be executed by the CPU 210 and is loaded from the storage 260, the control programs loaded from the storage unit 26, input or output data, parameters and the like.

The storage 260 is composed of an HDD (Hard Disc Drive), a nonvolatile semiconductor memory or the like, and stores the system program to be executed by the CPU 210, the various types of processing programs corresponding to the system program, the processing results and the like.

Further, the storage 260 has a storage medium (illustration is omitted) in which programs and data are stored. The storage medium is composed of a magnetic storage medium, an optical storage medium or a semiconductor memory, and is to be attached to the storage 260 either fixedly or detachably. These various types of programs are stored in a form of readable program codes, and the CPU 210 sequentially executes operation according to the program codes.

Further, the storage 260 stores a radiographing order information file 261 for storing radiographing order information received from either the information management apparatus 60 or the portable terminal 10. Here, since a data structure of the radiographing order information file 261 is approximately the same as the above-described radiographing order information file 161, illustration and description in detail thereof are omitted.

The I/F 270 is an interface to connect the controller 20 and the communication terminal 10-1. When the I/F 270 detects the portable terminal 10 is attached to the communication terminal 10-1, the I/F 270 transmits a detection signal to the CPU 210. Further, the I/F 270 adjusts transfer speed of data and concerts a data format between the controller 20 and the portable terminal 10. In other words, the I/F 270 mediates data exchange between the controller 20 and the portable terminal 10. For example, the I/F 270 transmits radiographing order information to the portable terminal 10 before radiography is performed. Moreover, the I/F 270 receives radiographing order information and a cassette ID corresponding to the radiographing order information from the portable terminal 10 after the radiography is completed.

Next, operation of the second embodiment will be described.

Here, a program in order to achieve each function written in a flowchart which will be described later is stored in either the storage 160 of the portable terminal 10 or the storage 260 of the controller 20 in a form of readable program codes by a computer, and either the CPU 110 of the portable terminal 10 or the CPU 210 of the controller 20 sequentially executes operation according to the program codes.

First, as a preparation process for performing radiography, a radiography preparation process for making the portable terminal 10 obtain radiographing order information from the controller 20 in a radiographic room will be described.

Figure 23:
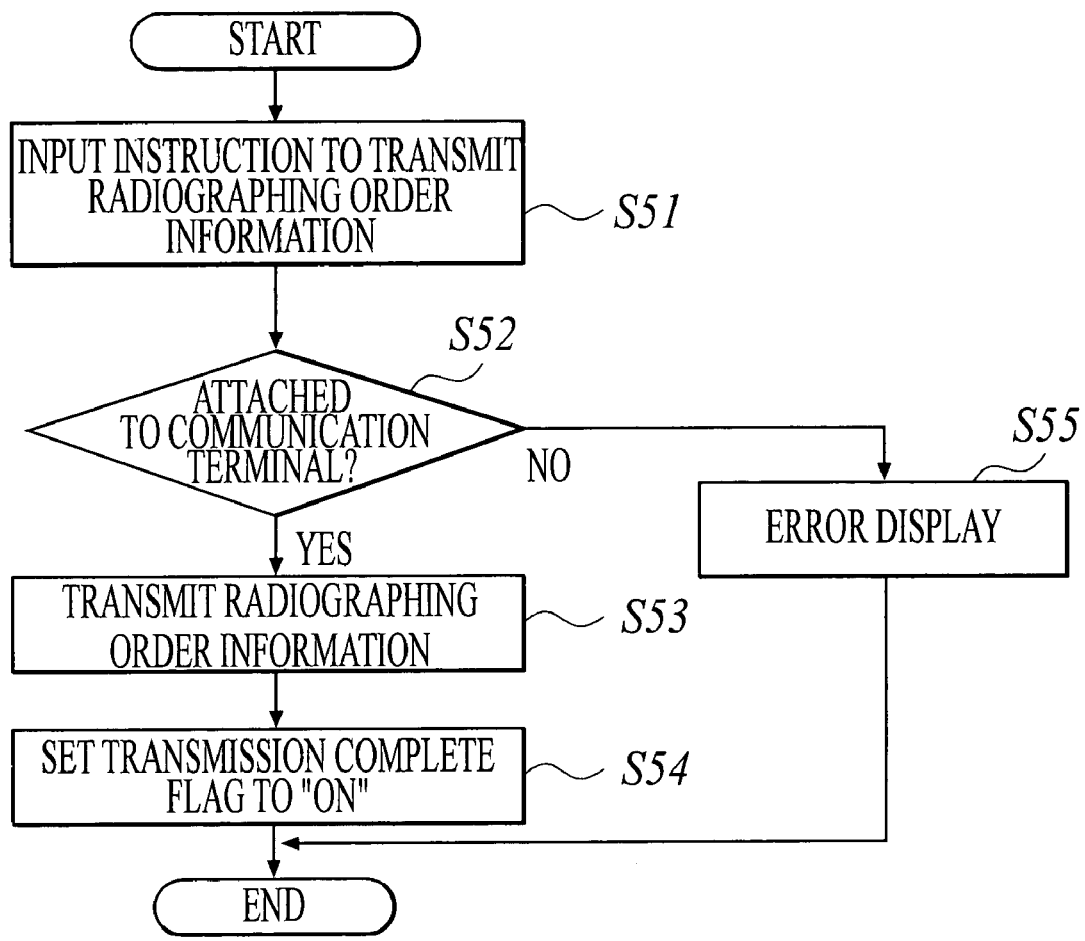
FIG. 23 is a flowchart illustrating a radiography preparation process executed by a CPU 210 of the controller 20.

FIG. 23 is a flowchart illustrating the radiography preparation process executed by the CPU 210 of the controller 20. As shown in FIG. 23, when an operator inputs transmission designation of radiographing order information at the input unit 220 (Step S51), the CPU 210 controls the communication control unit 240 to judge whether the portable terminal 10 is attached to the communication terminal 10-1 (Step S52). Here, if the portable terminal 10 is not attached to the communication terminal 10-1 (Step S52; NO), the CPU 210 displays a error message on the display unit 230 and terminates the radiography preparation process.

On the other hand, if the portable terminal 10 is attached to the communication terminal 10-1 (Step S52; YES), the CPU 210 obtains radiographing order information from the storage 260 and transmits the radiographing order information to the portable terminal 10 through the communication terminal 10-1 (Step S53). Then, the CPU 210 sets a transmission flag of the transmitted radiographing order information to "ON" (Step S54), and completes the radiography preparation process.

Figure 24:
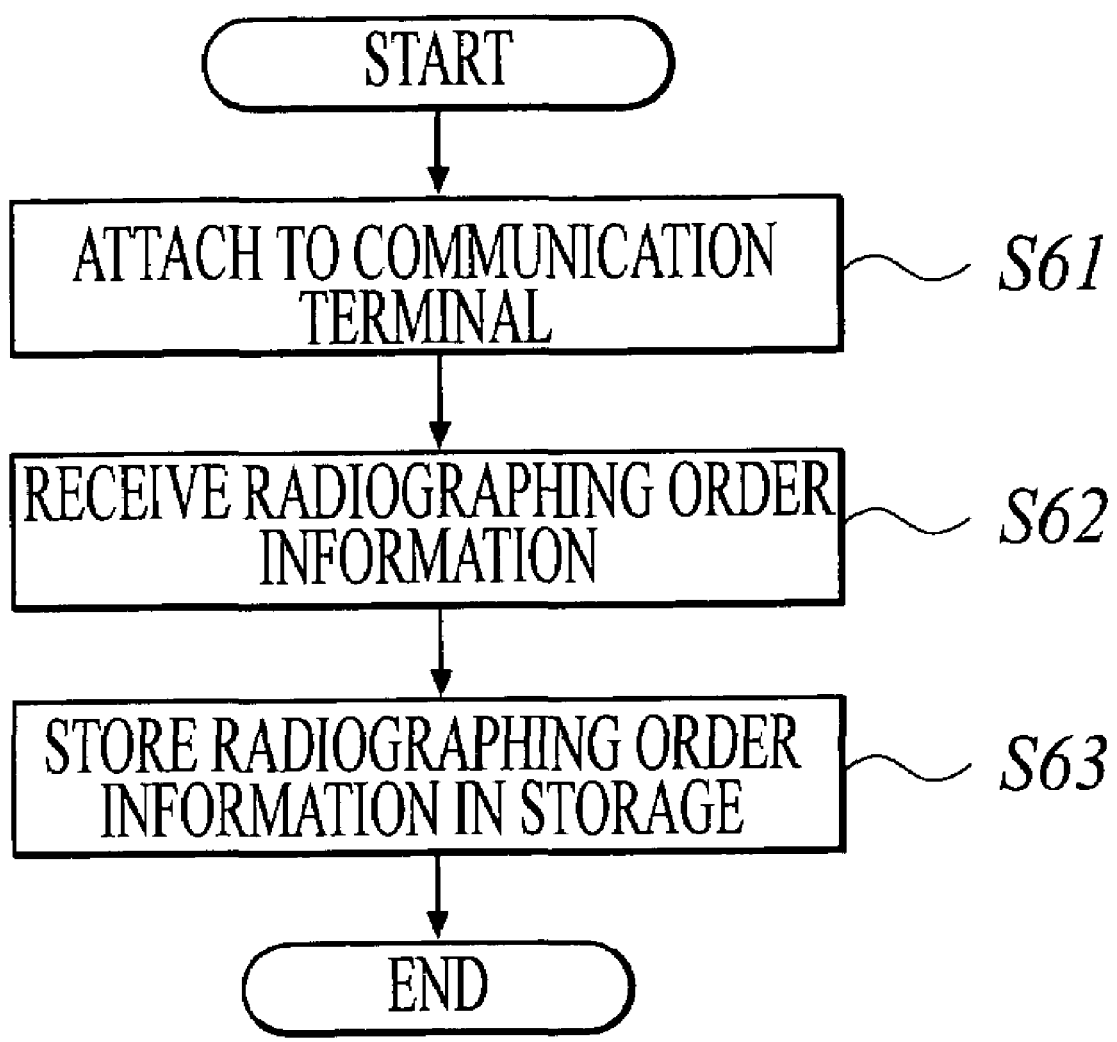
FIG. 24 is a flowchart illustrating a radiography preparation process executed by a CPU 110 of the portable terminal 10.

FIG. 24 is a flowchart illustrating a radiography preparation process executed by the CPU 110 of the portable terminal 10. As shown in FIG. 24, the portable terminal 10 is attached to the communication terminal 10-1 for obtaining radiographing order information (Step S61).

Next, the CPU 110 controls the I/F 140 to receive the radiographing order information transmitted from the controller 20 (Step S62). Then, the CPU 110 stores the received radiographing order information in the radiographing order information file 161 of the storage 160 (Step S63), and completes the radiographing order information obtaining process.

In the above-mentioned radiography preparation process, a display screen displayed on the display unit 230 of the controller 20 will be described with reference to FIG. 10 to FIG. 13.

FIGS. 10A and 10B are views showing menu screens 631 and 632 for selecting a desirable process. As shown in FIGS. 10A and 10B, in the menu screens 631 and 632, designation buttons for designating each menu of "SYSTEM STATUS", "OPERATOR SELECTION", "EXAMINATION HISTORY", "UTILITY", "VIEW FORMAT" and "OPERATION MODE" are placed as system menus. Further, within the designation buttons of "VIEW FORMAT" and "OPERATION MODE", input items are placed, and, for example, as shown in FIG. 10A, if "NORMAL" is inputted in the input item of "OPERATION MODE", a normal mode screen in the case of radiographing in a normal radiographic room is displayed and the following processes are performed under the normal mode. On the other hand, as shown in FIG. 10B, if "PORTABLE" is inputted in the input item of "OPERATION MODE" and the designation button is selected, a portable mode screen in the case of performing radiography with the use of the portable radiographing apparatus 40 is displayed, and the following processes are performed under the portable mode.

FIG. 13A is a view showing a portable list screen 635 in which radiographing order information is displayed as a list. As shown in FIG. 13A, in the portable list screen 635, placed are an area for displaying radiographing order information and an area for displaying a designation button for inputting various types of designation. In the area for displaying radiographing order information, placed are items for displaying patient ID, transmission tab type, name, sex, date of birth, radiographic part, radiographing count and pending as a part of radiographing order information. In each item, corresponding data is displayed respectively.

Further, at the right end and bottom end of the portable list screen 635, within an area for displaying designation buttons for inputting various types of designation, designation buttons on which text data of "TRANSMIT", "RECEIVE", "NEW/SEARCH", "MODIFY", "DELETE", . . . , "CONFIRMATION SCREEN" are displayed in addition to selection keys. By operating each designation button at the input unit 22, corresponding designation is inputted. For example, if radiographing order information displayed in the portable list screen 635 is selected with the selection key and the designation button "TRANSMIT" is operated, the selected radiographing order information is transmitted to the portable terminal 10. Here, when the radiographing order information is transmitted to the portable terminal 10, a transmission completion flag of the radiographing order information is set to "ON", and in the item of "TRANSMISSION TAB", a check flag "→" of completed transmission is displayed. Further, if the designation button "NEW/SEARCH" is operated, the input screen 633 is displayed for newly registering radiographing order information.

FIGS. 11 and 12 are views showing the input screens 633 and 634 which are displayed when the designation button "NEW/SEARCH" is operated in the above-described screen 635.

FIG. 11 is a view showing the input screen 633 for newly inputting patient information among radiographing order information. As shown in FIG. 11, in the screen 633, an area for inputting patient information and an area displaying letter keys for inputting letters are placed.

In the area for inputting patient information display at the upper part of the screen 633, items for inputting patient ID, patient name (roman character, kana, kanji), sex, date of birth and comments are placed, and according to operation at the input unit 220, input data is displayed in the corresponding item. Further, in the area displaying letter keys for inputting letters, a key input corresponding to the displayed letter keys is made with the use of a mouse or a touch panel comprised in the input unit 220. Here, the key input may be made with the use of the keyboard comprised in the input unit 220.

FIG. 12 is a view showing the screen 634 for newly inputting radiography information of radiographing order information. In the screen 634, placed are an area for displaying a designation button to designate a radiographic part as a radiography condition, an area for displaying a designation button to designate a radiographing direction at the radiographic part, and an area for displaying the inputted radiographic part and radiographing direction.

In an area displaying the designation button of radiographic part displayed at the upper left of the input screen 634, for example, designation buttons displaying text data of "HEAD", "NECK", . . . , "TEST" are placed, and by selecting each designation button at the input unit 220, the corresponding radiographic part is selected. Further, an area displaying the designation button of a radiographing direction displayed at the middle left of the input screen 634 is displayed with mesh, and therefore it is not possible to make a selection in the area under a portable mode. In other words, the radiographic parts displayed in the area are meant to be unselectable radiographic parts to perform radiography with the use of the portable radiographing apparatus 40. Here, as a method of displaying an unselectable state, other than displaying with mesh, it is possible to use a method of not displaying such area, or displaying such area as non-active. Further, warning may be output with sound or an image when the unselectable designation button is selected. Further, in an area displaying designation buttons of radiographing directions displayed at the bottom left of the input screen 634, for example, designation buttons on which text data "OBLIQUE", . . . , "PNEUMOCONIOSIS" as radiographing directions of the radiographic part "CHEST ETC" is displayed are placed, and by selecting each designation button at the input unit 220, the corresponding radiographing direction is selected. Further, in an area displaying radiographic parts and radiographing direction at the right side of the input screen 634, a radiographic part and a radiographing direction selected by designating the above-mentioned designation button are displayed, for example, as "CHEST ETC OBLIQUE".

Subsequently, a radiography start process in which the portable terminal 10 sets correspondence among a patient ID, a cassette ID and radiographing order information in a hospital room to be used for radiography before the start of radiography will be described.

Figure 25:
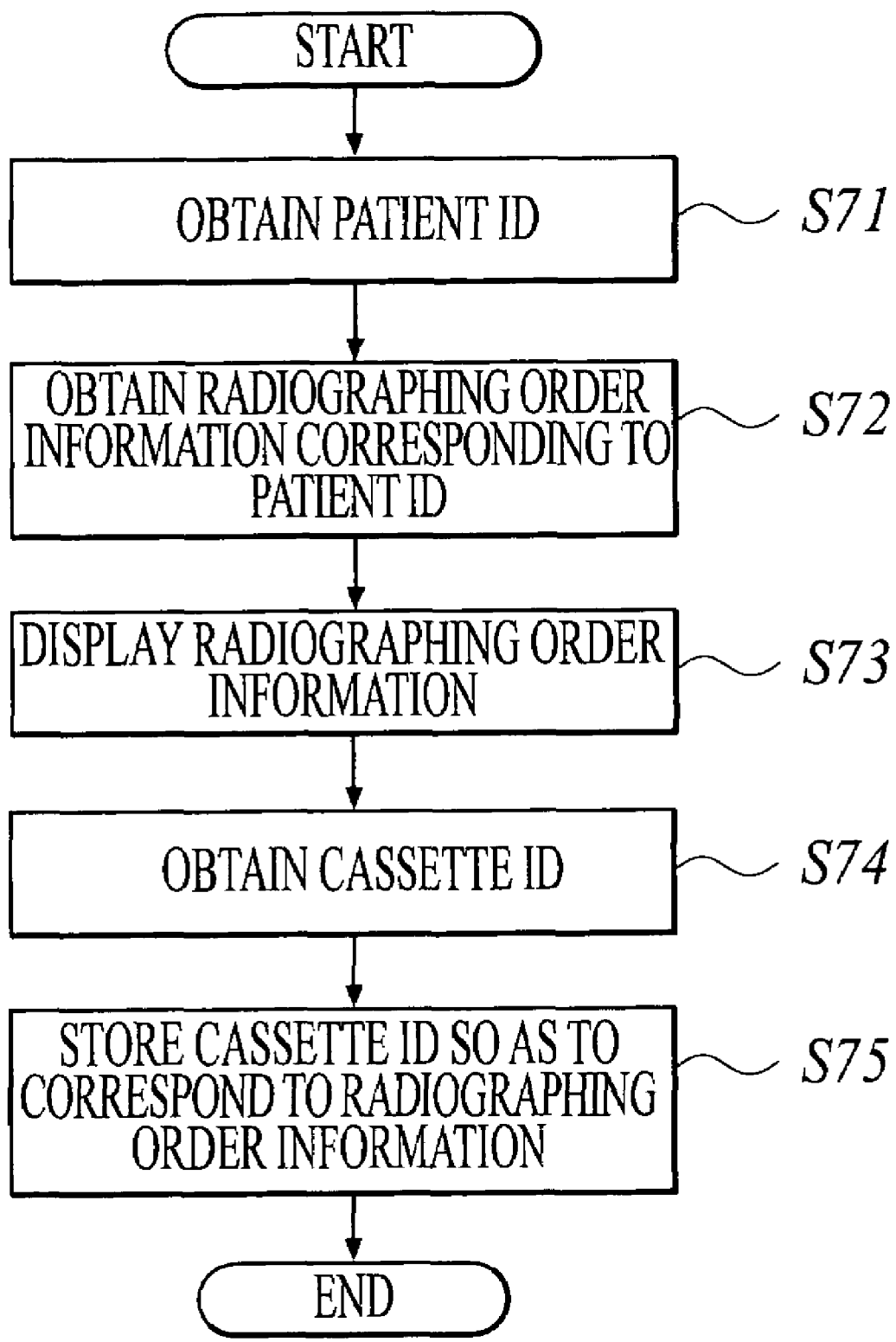
FIG. 25 is a flowchart illustrating a radiography start process executed by the CPU 110 of the portable terminal 10.

FIG. 25 is a flowchart illustrating the radiography start process executed by the CPU 110 of the portable terminal 10. As shown in FIG. 25, the CPU 110 controls the barcode reader 170 to read a barcode attached to either a bedside of a patient or a part of a patient body for obtaining a patient ID (Step S71). Next, the CPU 110 obtains radiographing order information corresponding to the read patient ID from the storage 160 (Step S72).

Subsequently, the CPU 110 displays the obtained radiographing order information on the display unit 130 (Step S73), and controls the barcode reader 170 to read a barcode attached to the cassette 50 for obtaining a cassette ID (Step S74). Then, the CPU 110 stores the obtained cassette ID in the storage 160 so as to be corresponded to the radiographing order information (Step S75), and completes the radiography start process.

In the above-mentioned radiography start process, a display screen displayed on the display unit 130 of the portable terminal 10 will be described with reference to FIGS. 9A and 9B. FIG. 9A is a view showing a patient list screen 431 displaying patients registered in the portable terminal 10 as a list. As shown in FIG. 9A, in the patient list screen 431, an area A1 for indicating patient information is placed, and in this area, items A2 for displaying patient ID, patient name and hospital room are placed. Concretely, in the item of patient ID, numeric data "0001" is displayed, and in the item of patient name, text data "ICHIRO YAMADA" is displayed.

FIG. 9B is a view showing a display screen 432 in which, when the barcode reader 170 of the portable terminal 10 obtains a patient ID, radiographing order information of the corresponding patient is displayed. As shown in FIG. 9B, in the display screen 432, an area A3 for displaying patient information and an area A4 for displaying radiography information are placed. In the area A3 for displaying patient information, items for displaying patient name, patient ID, sex, age, hospital room and hospital room are placed, and corresponding data is displayed within each item.

Further, in the area A4 for displaying radiography information, items for displaying radiographic part and cassette ID are placed. In the item of cassette ID, data obtained by the barcode reader 17 of the portable terminal 10 is displayed at the same time of being read. Concretely in the item of radiographic part, text data of "CHEST ETC OBLIQUE" is displayed, and in the item of cassette ID, numeric data of "04000108022016" is displayed.

Subsequently, as a process characteristic to the second embodiment of the present invention, a radiography completion post process in which a cassette ID corresponding to radiographing order information of which radiography has been performed in a radiographic room is transmitted to the controller after the radiography is completed will be described.

Figure 26:
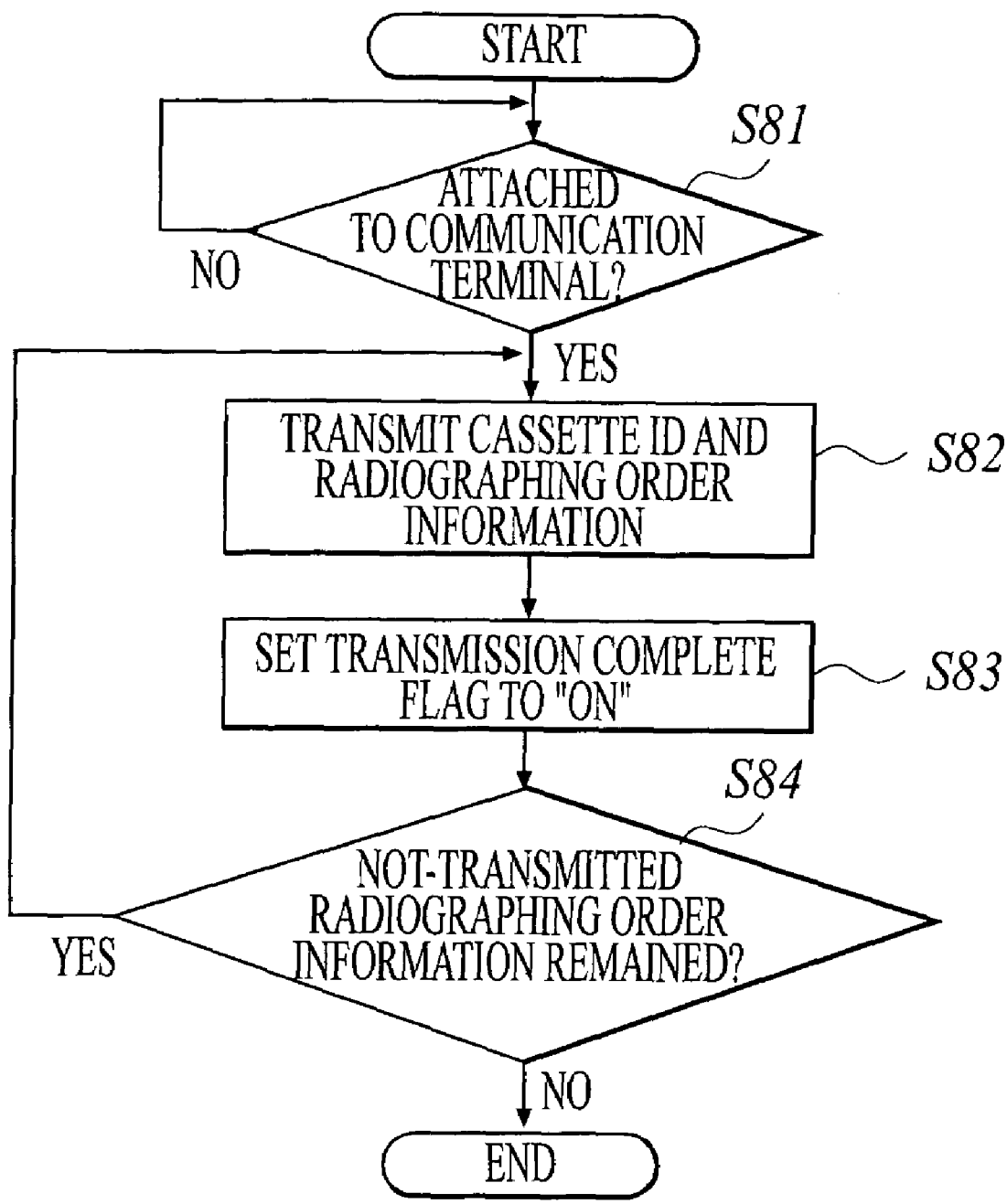
FIG. 26 is a flowchart illustrating a radiography completion post process executed by the CPU 110 of the portable terminal 10.

FIG. 26 is a flowchart illustrating the radiography completion post process executed by the CPU 110 of the portable terminal 10. As shown in FIG. 26, according to a detection signal outputted from the communication terminal 10-1, the CPU 110 judges whether the portable terminal 10 is attached to the communication terminal 10-1 (Step S81). If the portable terminal 10 is attached to the communication terminal 10-1 (Step S81; YES), the CPU 110 obtains a cassette ID corresponding to radiographing order information from the storage 160 and transmits the cassette ID to the controller 20 (Step S82).

Here, the radiographing order information transmitted from the controller 20% to the portable terminal 10 preferably includes a transmission destination of the cassette ID corresponding to the radiographing order information (for example, an IP address for identifying a computer (a controller or the like) on the network or the like). In other words, since the communication terminal 10-1 is capable of transmitting information to each of controllers 20 connected to the network N, the CPU 110 of the portable terminal 10 that has detected the attachment to the communication terminal 10-1 obtains the transmission destination from the radiographing order information, and transmits the radiographing order information and the cassette ID to the controller 20 corresponding to the obtained transmission destination.

Here, in the radiography preparation process, the portable terminal 10 may store identification information of the controller 20 that has originally received radiographing order information, and if the radiographing order information received from the controller 20 does not include a transmission destination, the portable terminal 10 may transmits the radiographing order information and the cassette ID to the controller 20 that has originally received the radiographing order information. Or, a transmission destination may be inputted at the operation unit 120 of the portable terminal 10, and necessary information may be transmitted to the designated transmission destination.

Next, regarding the radiographing order information of the transmitted cassette ID, the CPU 110 sets a transmission completion flag to "ON" (Step S83). Further, the CPU 110 judges whether there is remaining radiographing order information which has not been transmitted among the radiographing order information stored in the radiographing order information file 161 (Step S84). If there is remaining radiographing order information which has not been transmitted (Step S84; YES), the CPU 110 proceeds to Step S82 to execute the above-mentioned processes repeatedly. On the other hand, if, regarding all the radiographing order information stored in the radiographing order information file 161, the radiographing order information and the cassette ID has been transmitted (Step S84; NO), the CPU 110 completes the radiography completion post process.

FIG. 27 is a flowchart illustrating a radiography completion post process executed by the CPU 210 of the controller 20. As shown in FIG. 27, when the CPU 21 receives a cassette ID corresponding to radiographing order information from the portable terminal 10 through the communication terminal 10-1 (Step S91), the CPU 210 sets a setting mode, to a portable mode. Here, the setting of the portable mode may be set according to designation inputted at the input unit 220.

Next, the CPU 210 stores the received cassette ID in the radiographing order information file 261 with the radiographing order information correspondingly (Step S92), and the CPU 210 sets a transmission completion flag to "ON" regarding the radiographing order information of the received cassette ID (Step S93). Subsequently, the CPU 210 transmits the radiographing order information and the cassette ID so as to correspond to each other, to the information management apparatus 60 (Step S94).

Further, the CPU 210 judges whether a medical image and a cassette ID have been received from the medical image reading apparatus 30 (Step S95). If the medical image and the cassette ID have been received (Step S95; YES), based on the cassette ID, the CPU 210 stores in the storage 260, the radiographing order information and the medical image so as to correspond to each other (Step S96). Then, the CPU 210 displays the medical image corresponding to the radiographing order information received from the portable terminal 10 on the display unit 230 under the portable mode (step S97), and completes the radiography completion post process.

Next, with reference to FIG. 17, a medical image displayed on the display unit 230 of the controller 20 will be described. FIG. 17 is a view showing a portable process screen 639, which is displayed on the display unit 230 when radiography is performed with the use of the portable terminal 10. As shown in FIG. 17, the portable process screen 639 has a structure where medical images of a plurality of patients registered in the same portable terminal 10 are displayed on the same screen.

In other words, in the portable process screen 639, an area B27 for displaying operator information and areas B28, B29 and B30 for displaying patient information, a medical image and radiography information at each patient are placed. In the same screen, it is possible to display as many as four types of medical images. Concretely, at the area B27 for displaying the operator information at the upper left of the portable process screen 639, an item for displaying text data "TARO SUZUKI" as an operator name is placed. Further, as a medical image displayed at each patient, to describe the medical image displayed at the left end, at the area B28 for displaying the patient information, an item for displaying numeric data of "0001" as a patient ID and in item for displaying text data of "ICHIRO YAMADA" as a name are placed.

At its below, the area B29 for displaying a medical image is placed, and within this area, an item for displaying the medical image and numeric data of "170" as a reading apparatus ID, and an item for displaying text data of "NORMAL" as resolution are placed. Further, at its further below, the area B30 for displaying the radiography information is placed, and within this area, an item for displaying text data of "CHEST ETC OBLIQUE" as a radiographic part and an item for displaying numeric data "01000108022016" as a cassette ID are placed.

Figure 18:
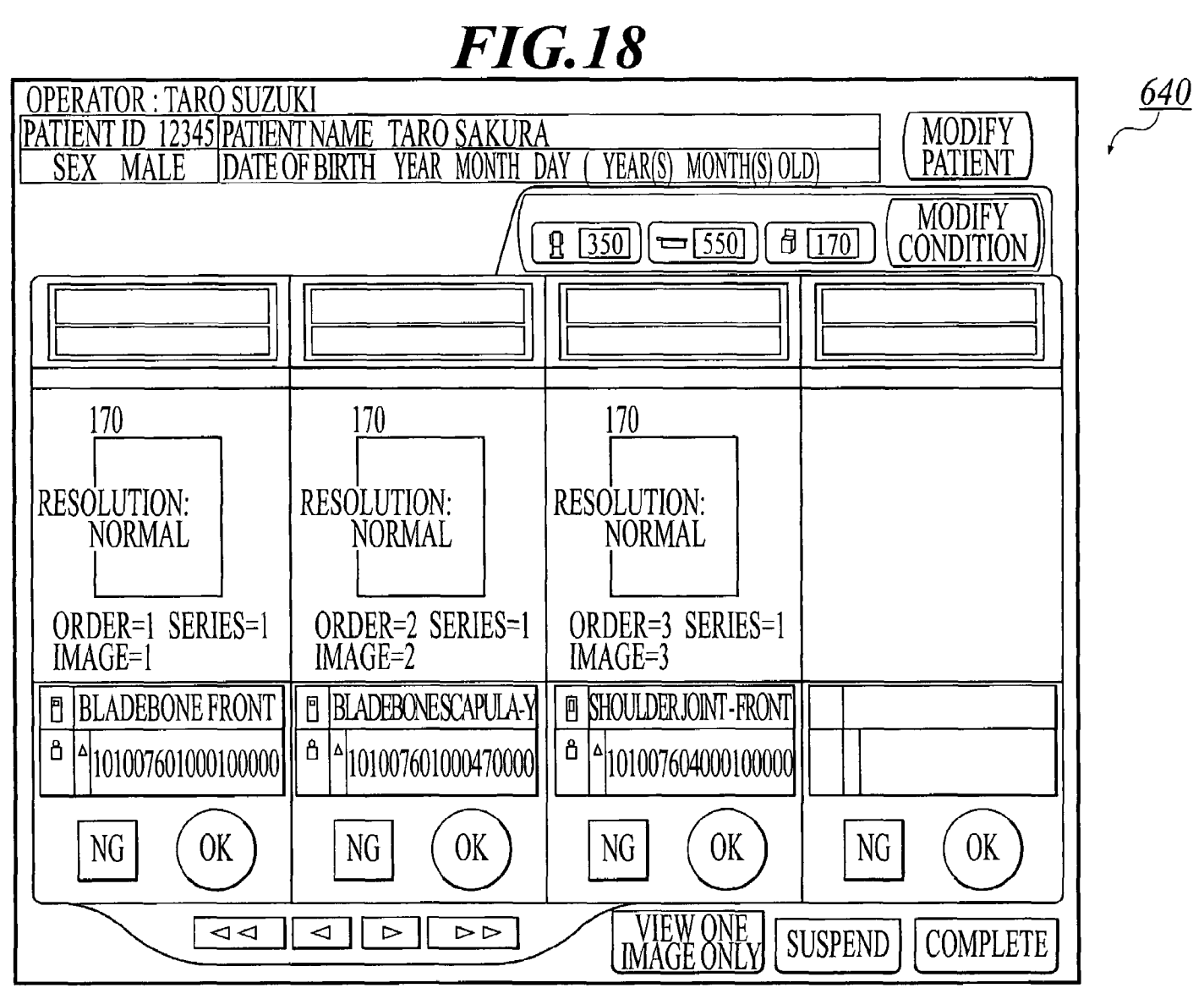

Here, if the controller 20 does not receive the radiographing order information and the cassette ID from the portable terminal 10, the controller 20 sets a mode to the normal mode, and displays a medical image radiographed in a radiographic room. Here, under the normal mode, if the medical image is displayed, a screen 640 shown in FIG. 18 is displayed on the display unit 230. In other words, regarding a medical image radiographed in a radiographic room, since it is possible to display a medical image at each time that radiography on one patient is completed, a medical image is displayed at each radiographed patient.

As mentioned, according to the medical image radiographing system 200 in the second embodiment, after radiography is performed, the portable terminal 10 transmits the radiographing order information and the cassette ID stored in the radiographing order information file 161 to the controller 20. When the controller 20 receives the cassette ID corresponding to the radiographing order information, the controller 20 sets a mode to the portable mode and stores the received cassette ID with the radiographing order information correspondingly. Further, the controller 20 receives a medical image and a cassette ID from the medical image reading apparatus 30 and sets correspondence between the radiographing order information and the medical image based on the cassette ID. Then, the controller 20 displays medical images corresponding to the plurality of radiographing order information received from the same portable terminal, over a plurality of patients on the display unit 230.

Therefore, if medical images of a plurality of patients are radiographed at round visits, since it is possible to simultaneously display medical images corresponding to the radiographing order information stored in the same portable terminal 10, it is not necessary to operate the portable terminal 10 for each of the plurality of patients, and it is possible to improve operationality by omitting labor of the operation to display a medical image. Further, when the controller 20 receives radiographing order information and a cassette ID from the portable terminal 10, the controller 20 automatically sets a mode to the portable mode and displays a medical image corresponding to the radiographing order information received from the portable terminal 10 under the portable mode. Therefore, it is possible to omit labor of setting a mode, and thereby it is convenient.

Further, in the second embodiment, regarding a medical image radiographed in a normal radiographic room, the image process screen 640 (see FIG. 18) displaying medical images at each patient is displayed under a normal mode. Regarding a medical image radiographed at round visits with the use of the portable radiographing apparatus 40, the image process screen 639 (see FIG. 17) displaying medical images over a plurality of patients is displayed under a portable mode. Thereby, it is possible for an operator to perform an image process while clearly recognizing whether the displayed image is radiographed in a radiographic room or with the use of the portable radiographing apparatus 40, and therefore the operation can be done under good operationality. Further, since it is possible to display a medical image suitably according to a radiography mode, it is possible to effectively display a medical image to perform an image process.

Here, the description above in the second embodiment is one example of a suitable medical image radiographing system and a suitable method for managing a medical image according to the present invention, and the present invention is not limited to the description.

For example, the above-described system structure of the medical image radiographing system 200 is one example, and a system structure of the present invention is not limited to the description above. As a medical image radiographing system 100 shown in FIG. 1, the portable terminal 10 and the communication terminal 10-1 which controls communication between the portable terminal and the controller 20 may be directly connected to the controller 20. According to such structure, if a system change is needed, it is easy to reconstruct the system by benefiting from a large flexibility of the system change. For example, if the portable terminal 10 is to be installed to the conventional medical image radiographing system, since it is only necessary to change systems of the portable terminal 10 and the controller 20, it is possible to omit cost and labor at the system installation. Further, it is also possible to immediately deal with a version-up of the system of the like, it is convenient. Further, by directly connecting between the portable terminal 10 and the controller 20, it is possible to prevent information from leaking, and thereby it is possible to establish communication with high security.

Further, the above-described structure of the display screen is one example, and a structure of the present invention is not limited to the description above. For example, the description has been made with the structure where as many as four types of medical images can be displayed on the image process screen. However, a structure where more than four types of medical images can be displayed, and a structure where less than four types of medical images can be displayed are also acceptable. Or, a structure where all the medical images corresponding to the radiographing order information received from the same portable terminal 10 can be displayed on the same display screen is also acceptable. In this case, since all the medical images are displayed on the display unit 230, a structure where reduced images such as a thumbnail or the like are displayed is also acceptable.

Thereby, since it is possible to simultaneously confirm all the medical images radiographed at round visits, it is possible to minimize oversight on a medical image, misreception of radiographing order information, a lapse of radiography and the like. Further, under a portable mode, since a reduced image of the medical image is displayed, it is possible to accurately recognize the radiography mode from the screen structure. Thereby, an operator can perform an appropriate process while always recognizing a workflow being performed currently. Further, a structure where a magnified medical image is displayed by operating a medical image displayed as a thumbnail or the like is also acceptable. In this case, it is possible to display a detailed medical image immediately, and thereby it is possible to improve visibility.

Further, the description has been made with the case that the controller 20 automatically sets a mode to a normal mode or a portable mode depending on whether there is reception of radiographing order information from the portable terminal 10. However, for example, a structure where an operator sets each mode at the menu screen is also acceptable.

Further, the cassette ID transmitted with the radiographing order information correspondingly may be in any shape as long as its correspondence to the radiographing order information is precise. In other words, a structure where a cassette ID is transmitted along with radiographing order information is also acceptable. Further, a structure where a cassette ID is transmitted along with a radiographing ID uniquely allocated to radiographing order information is also acceptable.

And so forth, the structure detail and the operation detail of each component of the medical image radiographing system 200 in the second embodiment can accordingly be changed without departing the gist of the present invention.

The entire disclosure of Japanese Patent Application No. Tokugan 2003-92443 filed on Mar. 28, 2003 and No. Tokugan 2003-84836 filed on Mar. 26, 2003 including specifications, claims, drawings and summaries are incorporated herein by reference in their entirety.

What is claimed is:

1. A medical image radiographing system comprising:
a radiographic-room-use radiographing apparatus for performing medical radiography on a predetermined part of a patient in a radiographic room;
a portable radiographing apparatus, which is movable, for performing medical radiography on a predetermined part of the patient at a bedside of the patient; and
a controller for displaying an input screen corresponding to inputted information and for inputting information through the input screen,
wherein, when radiographing order information for performing the medical radiography is inputted, the controller displays a selection input screen for inputting a selection of whether the radiographing order information is for the medical radiography to be performed by the radiographic-room-use radiographing apparatus or the medical radiography to be performed by the portable radiographing apparatus, and the controller displays a radiographing order information input screen differently in accordance with the inputted selection, and
wherein at completion of inputting of the radiographing order information, the controller displays a same confirmation input screen for inputting confirmation of the completion of the inputting of the radiographing order information regardless of whether the radiographing order information is for the medical radiography to be performed by the radiographic-room-use radiographing apparatus or the medical radiography to be performed by the portable radiographing apparatus.

2. The system of claim 1, wherein the radiographing order information input screen comprises an input screen for inputting the radiographing order information including a radiographing condition of the patient.

3. The system of claim 2, wherein, when the inputted selection inputted is for the portable radiographing apparatus, the input screen displayed by the controller comprises an input screen for inputting the radiographing condition that is displayed when the inputted selection is for the radiographic-room-use radiographing apparatus, with an effect added to the input screen to indicate that at least one predetermined portion of the input screen is not applicable to the portable radiographing apparatus.

4. The system of claim 3, wherein the effect added to the input screen comprises hatching displayed over at least one portion of the input screen corresponding to at least one radiographing condition under which the portable radiographing apparatus is not usable.

5. A method for managing a medical image with a medical image radiographing system comprising a radiographic-room-use radiographing apparatus for performing medical radiography on a predetermined part of a patient in a radiographic room, a portable radiographing apparatus, which is movable, for performing medical radiography on a predetermined part of the patient at a bedside of the patient, and a controller for displaying an input screen corresponding to inputted information and for inputting information through the input screen, said method comprising:

displaying, when radiographing order information is inputted for performing the medical radiography, a selection input screen for inputting selection of whether the radiographing order information is for the medical radiography to be performed by the radiographic-room-use radiographing apparatus or the medical radiography to be performed by the portable radiographing apparatus;

displaying a radiographing order information input screen differently in accordance with the inputted selection; and displaying, at completion of inputting of the radiographing order information, a same confirmation input screen for inputting confirmation of the completion of the inputting of the radiographing order information regardless of whether the radiographing order information is for the medical radiography to be performed by the radiographic-room-use radiographing apparatus or the medical radiography to be performed by the portable radiographing apparatus.

6. The method of claim 5, wherein the radiographing order information input screen comprises an input screen for inputting the radiographing order information including a radiographing condition of the patient.

7. The method of claim 6, wherein, when the inputted selection inputted is for the portable radiographing apparatus, the displayed input screen for inputting the radiographing order information comprises an input screen for inputting the radiographing condition that is displayed when the inputted selection is for the radiographic-room-use radiographing apparatus, with an effect added to the input screen to indicate that at least one predetermined portion of the input screen is not applicable to the portable radiographing apparatus.

8. The method of claim 7, wherein the effect added to the input screen comprises hatching displayed over at least one portion of the input screen corresponding to at least one radiographing condition under which the portable radiographing apparatus is not usable.

9. A medical image radiographing system comprising:
a controller for managing radiographing order information and a medical image so as to correspond to each other;
a portable terminal for storing the radiographing order information and identification information of a cassette so as to correspond to each other; and
a medical image reading apparatus for reading out the medical image from the cassette and the identification information of the cassette,
wherein the controller, the portable terminal and the medical image reading apparatus are connected through a network,
wherein the portable terminal comprises:
a storage section for storing the radiographing order information and the identification information of the cassette so as to correspond to each other; and
a communication section for transmitting the radiographing order information and the identification information of the cassette so as to correspond to each other;
wherein the medical image reading apparatus comprises:
a communication section for transmitting the medical image read out from the cassette and the identification information of the cassette so as to correspond to each other, and
wherein the controller comprises:
a communication section for receiving a set of the radiographing order information and the identification information of the cassette, and a set of the identification information of the cassette and the medical image;
a storage section for storing the radiographing order information and the medical image so as to correspond to each other based on the identification information of the cassette; and
a display control section for displaying at least two medical images corresponding to a plurality of patients on a same screen, when the at least two medical images are among medical images that corresponding to radiographing order information that is received from a same portable terminal.

10. The system of claim 9, wherein in the controller:
the communication section receives a set of the identification information of the cassette and radiographing order information corresponding to a plurality of patients, and a set of the indentification information of the cassette and a plurality of medical images corresponding to the plurality of patients that are read from the cassette;
the storage section stores the radiographing order information of the plurality of patients and the medical images of the plurality of patients so as to correspond to each other based on the identification information of the cassette; and
the display control section displays at least two medical images corresponding to the plurality of patients among the medical images corresponding to the radiographing order information of the plurality of patients received from the same portable terminal, on the same screen.

11. The system of claim 9, wherein the controller comprises a mode setting section for setting one of a normal mode under which a medical image radiographed in a radiographic room is displayed and a portable mode under which a medical image radiographed at round visits is displayed, and wherein the display control section operates in accordance with a mode set by the mode setting section.

12. The system of claim 11, wherein the display control section of the controller displays at least one medical image of a same patient on the same screen under the normal mode, and the display control section of the controller displays at least one medical image corresponding to radiographing order information stored in a same portable terminal under the portable mode.

13. The system of claim 11, wherein in the portable terminal:

the storage section stores the radiographing order information regarding the radiography at the round visits and the identification information of the cassette; and the communication section transmits the radiographing order information regarding the radiography at the round visits and the identification information of the cassette, and wherein in the controller:

the communication section receives the radiographing order information regarding the radiography at the round visits and the identification information of the cassette;

the mode setting section sets the portable mode when the communication section receives the radiographing order information regarding the radiography at the round visits and the identification information of the cassette; and the display control section operates under the portable mode.

14. A medical image radiographing system comprising:

a controller for managing a medical image, identification information of a cassette and radiographing order information so as to correspond to each other;

a portable terminal for storing the radiographing order information and the identification information of the cassette so as to correspond to each other; and a medical image reading apparatus for reading out the medical image from the cassette and the identification information of the cassette, wherein the controller, the portable terminal and the medical image reading apparatus are connected through a network, wherein the portable terminal comprises:

a storage section which stores the radiographing order information and the identification information of the cassette so as to correspond to each other; and a communication section for transmitting the radiographing order information and the identification information of the cassette so as to correspond to each other, wherein the medical image reading apparatus comprises:

a communication section for transmitting the medical image read out from the cassette and the identification information of the cassette so as to correspond to each other, and wherein the controller comprises:

a communication section for receiving a set of the radiographing order information and the identification information of the cassette, and a set of the medical image and the identification information of the cassette;

a storage section for storing the radiographing order information and the medical image so as to correspond to each other based on the identification information of the cassette;

a mode setting section for setting one of a normal mode under which a medical image radiographed in a radiographic room is displayed and a portable mode under which a medical image radiographed at round visits is displayed; and a display control section for displaying at least one medical image of a same patient on a same screen under the normal mode, and for displaying at least two medical images corresponding to a plurality of patients on a same screen, when the at least two medical images are among medical images that correspond to radiographing order information that is received from a same portable terminal under the portable mode.

15. The system of claim 14, wherein in the controller:

the communication section receives a set of the identification information of the cassette and a plurality of pieces of radiographing order information, and a set of the identification information of the cassette and a plurality of medical images; and the display control section displays all of the medical images corresponding to the plurality of pieces of radiographing order information received, on the same screen.

16. The system of claim 14, wherein in the controller:

the mode setting section sets the normal mode when the communication section does not receive the radiographing order information and the identification information of the cassette from the portable terminal, and sets the portable mode when the communication section receives the radiographing order information and the identification information of the cassette from the portable terminal; and the display control section operates under the mode set by the mode setting section.

17. A method for displaying a medical image in a medical image radiographing system in which: (i) a controller for managing radiographing order information and the medical image so as to correspond to each other, (ii) a portable terminal for storing the radiographing order information and identification information of a cassette so as to correspond to each other and (iii) a medical image reading apparatus for reading out the medical image from the cassette and the identification information of the cassette are connected through a network, said method comprising:

storing the radiographing order information and the identification information of the cassette so as to correspond to each other;

transmitting the radiographing order information and the identification information of the cassette so as to correspond to each other;

transmitting the medical image read out from the cassette and the identification information of the cassette so as to correspond to each other;

receiving a set of the radiographing order information and the identification information of the cassette, and a set of the medical image and the identification information of the cassette;

storing the radiographing order information and the medical image so as to correspond to each other based on the identification information of the cassette;

displaying at least two medical images corresponding to a plurality of patients on a same screen, when the at least two medical images are among medical images that correspond to radiographing order information that is received from a same portable terminal.

18. The method of claim 17, wherein:

said receiving comprises receiving a set of the identification information of the cassette and radiographing order information corresponding to a plurality of patients, and a set of the identification information of the cassette and medical images corresponding to the plurality of patients;

said storing the radiographing information and the medical image comprises storing the radiographing order information of the plurality of patients and the medical images of the plurality of patients so as to correspond to each other based on the identification information of the cassette; and said displaying comprises displaying on a same screen at least two medical images corresponding to the plurality of patients that are among the medical images corresponding to the radiographing order information of the plurality of patients received from the same portable terminal.

19. The method of claim 17, further comprising:

setting one of a normal mode under which a medical image radiographed in a radiographic room is displayed and a portable mode under which a medical image radiographed at round visits is displayed; and controlling a display screen to operate in accordance with a set mode.

20. The method of claim 19, wherein controlling the display screen comprises displaying at least one medical image of a same patient on the same screen under the normal mode, and displaying at least one medical image corresponding to radiographing order information stored in the same portable terminal on the same screen under the portable mode.

21. The method of claim 19, further comprising:

storing the radiographing order information regarding the radiography at the round visits and the identification information;

transmitting the radiographing order information regarding the radiography at the round visits and the identification information;

receiving the radiographing order information regarding the radiography at the round visits and the identification information;

setting the portable mode when the radiographing order information regarding the radiography at the round visits and the identification information are received; and displaying the medical image under the portable mode.

22. A method for displaying a medical image in a medical image radiographing system in which: (i) a controller for managing the medical image, identification information of a cassette and radiographing order information so as to correspond to each other, (ii) a portable terminal for storing the radiographing order information and the identification information of the cassette so as to correspond to each other, and (iii) a medical image reading apparatus for reading out the medical image from the cassette and the identification information of the cassette are connected through a network, comprising:

storing the radiographing order information and the identification information of the cassette so as to correspond to each other;

transmitting the radiographing order information and the identification information of the cassette so as to correspond to each other;

transmitting the medical image read out from the cassette and the identification information of the cassette so as to correspond to each other;

receiving a set of the radiographing order information and the identification information of the cassette, and a set of the medical image and the identification information of the cassette;

storing the radiographing order information and the medical image so as to correspond to each other based on the identification information of the cassette;

setting one of a normal mode under which a medical image radiographed in a radiographic room is displayed and a portable mode under which a medical image radiographed at round visits is displayed; and displaying at least one medical image of a same patient on a same screen under the normal mode, and displaying at least two medical images corresponding to a plurality of patients on a same screen, when the at least two medical images are among medical images that correspond to radiographing order information that is received from a same portable terminal under the portable mode.

23. The method of claim 22, wherein:

said receiving comprises receiving a set of the identification information of the cassette and a plurality of pieces of radiographing order information, and a set of the identification information of the cassette and a plurality of medical images; and said displaying comprises displaying all of the medical images corresponding to the plurality of pieces of radiographing order information received, on the same screen.

24. The method of claim 22, wherein the normal mode is set when the radiographing order information and the identification information of the cassette are not received, and the portable mode is set when the radiographing order information and the identification information of the cassette are received, and the displaying is controlled in accordance with a set mode.

25. A medical image radiographing system comprising:

a radiographic-room-use radiographing apparatus for performing medical radiography on a predetermined part of a patient in a radiographic room;

a portable radiographing apparatus, which is movable, for performing medical radiography on a predetermined part of the patient at a bedside of the patient;

a controller for displaying an input screen corresponding to inputted information and for inputting information through the input screen;

a portable terminal for storing radiographing order information and identification information of a cassette so as to correspond to each other; and a medical image reading apparatus for reading out the medical image from the cassette and the identification information of the cassette, wherein the controller comprises:

a display section for displaying, when the radiographing order information for performing the medical radiography is inputted, a selection input screen for inputting a selection of whether the radiographing order information is for the medical radiography to be performed by the radiographic-room-use radiographing apparatus or the medical radiography to be performed by the portable radiographing apparatus, for displaying a radiographing order information input screen differently in accordance with the inputted selection, and for displaying, at completion of inputting of the radiographing order information, a same confirmation input screen for inputting confirmation of the completion of the inputting of the radiographing order information regardless of whether the radiographing order information is for the medical radiography to be performed by the radiographic-room-use radiographing apparatus or the medical radiography to be performed by the portable radiographing apparatus;

a communication section for receiving a set of the radiographing order information and the identification information of the cassette, and a set of the medical image and the identification information of the cassette;

a storage section for storing the radiographing order information and the medical image so as to correspond to each other based on the identification information of the cassette; and a display control section for displaying at least two medical images corresponding to a plurality of patients on a same screen, when the at least two medical images are among medical images that correspond to radiographing order information that is received from a same portable terminal, wherein the portable terminal comprises:

a storage section for storing the radiographing order information and the identification information of the cassette so as to correspond to each other; and a communication section for transmitting the radiographing order information and the identification information of the cassette so as to correspond to each other, and wherein the medical image reading apparatus comprises:

a communication section for transmitting the medical image read out from the cassette and the identification information of the cassette so as to correspond to each other.

* * * * *